(12) United States Patent
Lanier et al.

(10) Patent No.: US 8,993,542 B2
(45) Date of Patent: Mar. 31, 2015

(54) METHODS OF TREATING VIRAL INFECTIONS

(75) Inventors: Ernest Randall Lanier, Chapel Hill, NC (US); Merrick R. Almond, Apex, NC (US); George R. Painter, Chapel Hill, NC (US)

(73) Assignee: Chimerix Inc., Durham, NC (US)

( * ) Notice: Subject to any disclaimer, the term of this patent is extended or adjusted under 35 U.S.C. 154(b) by 591 days.

(21) Appl. No.: 12/864,431

(22) PCT Filed: Jan. 23, 2009

(86) PCT No.: PCT/US2009/000447
§ 371 (c)(1),
(2), (4) Date: Oct. 5, 2010

(87) PCT Pub. No.: WO2009/094190
PCT Pub. Date: Jul. 30, 2009

(65) Prior Publication Data
US 2011/0021464 A1    Jan. 27, 2011

Related U.S. Application Data

(60) Provisional application No. 61/023,633, filed on Jan. 25, 2008, provisional application No. 61/101,810, filed on Oct. 1, 2008.

(51) Int. Cl.
*A61K 31/675* (2006.01)
*A61K 31/505* (2006.01)
(Continued)

(52) U.S. Cl.
CPC .............. *A61K 31/675* (2013.01); *A61K 31/706* (2013.01); *A61K 2300/00* (2013.01); *A61K 9/0014* (2013.01)
USPC ............................... 514/80; 514/256; 514/274

(58) Field of Classification Search
CPC ... A61K 31/67; A61K 31/706; A61K 31/506; A61K 2300/00
USPC ............................................ 514/80, 254, 274
See application file for complete search history.

(56) References Cited

U.S. PATENT DOCUMENTS

| | | | |
|---|---|---|---|
| 1,944,530 | A | 1/1934 | Schonburg |
| 3,422,021 | A | 1/1969 | Roy |

(Continued)

FOREIGN PATENT DOCUMENTS

| | | |
|---|---|---|
| CN | 1810816 A | 8/2006 |
| CS | 220713 B1 | 4/1983 |

(Continued)

OTHER PUBLICATIONS

Postma et al. "Cost-effectiveness of antenatal HIV-testing: reviewing its pharmaceutical and methodological aspects," Expert Opin. Pharmacother. 2004, vol. 5, No. 3, pp. 521-528.*

(Continued)

*Primary Examiner* — Shengjun Wang
(74) *Attorney, Agent, or Firm* — Cooley LLP; Ivor R. Elrifi; Heidi A. Erlacher

(57) ABSTRACT

The present invention provides methods of treating human immunodeficiency virus (HIV) and/or hepatitis B virus (HBV) infection, including administering a compound described in the invention in an amount effective treat the HIV and/or HBV infection and at least substantially inhibit the development of resistance to said antiviral compounds in the subject. Pharmaceutical compositions are also provided.

14 Claims, 3 Drawing Sheets

(51) Int. Cl.
*A61K 31/706* (2006.01)
*A61K 9/00* (2006.01)

(56) References Cited

U.S. PATENT DOCUMENTS

| | | |
|---|---|---|
| 3,468,935 A | 9/1969 | Peck |
| 4,327,039 A | 4/1982 | Blum et al. |
| 4,444,766 A | 4/1984 | Bosies et al. |
| 4,562,179 A | 12/1985 | Teraji et al. |
| 4,619,794 A | 10/1986 | Hauser |
| 4,705,651 A | 11/1987 | Staibano |
| 4,870,063 A | 9/1989 | Binderup et al. |
| 4,927,814 A | 5/1990 | Gall et al. |
| 5,043,437 A | 8/1991 | Khorlin et al. |
| 5,047,533 A | 9/1991 | Reist et al. |
| 5,142,051 A | 8/1992 | Holy et al. |
| 5,183,815 A | 2/1993 | Saari et al. |
| 5,194,654 A | 3/1993 | Hostetler et al. |
| 5,196,409 A | 3/1993 | Breuer et al. |
| 5,223,263 A | 6/1993 | Hostetler et al. |
| 5,247,085 A | 9/1993 | Harnden et al. |
| 5,300,671 A | 4/1994 | Tognella et al. |
| 5,300,687 A | 4/1994 | Schwender et al. |
| 5,312,954 A | 5/1994 | Breuer et al. |
| 5,395,826 A | 3/1995 | Naumann et al. |
| 5,411,947 A | 5/1995 | Hostetler et al. |
| 5,428,181 A | 6/1995 | Sugioka et al. |
| 5,442,101 A | 8/1995 | Hanhijarvi et al. |
| 5,463,092 A | 10/1995 | Hostetler et al. |
| 5,476,938 A | 12/1995 | Vemishetti et al. |
| 5,484,809 A | 1/1996 | Hostetler et al. |
| 5,484,911 A | 1/1996 | Hong et al. |
| 5,512,671 A | 4/1996 | Piantadosi et al. |
| 5,532,226 A | 7/1996 | Demarest et al. |
| 5,591,852 A | 1/1997 | Vemishetti et al. |
| 5,614,548 A | 3/1997 | Piantadosi et al. |
| 5,627,185 A | 5/1997 | Gosselin et al. |
| 5,650,510 A | 7/1997 | Webb, II et al. |
| 5,656,745 A | 8/1997 | Bischofberger et al. |
| 5,663,159 A | 9/1997 | Starrett, Jr. et al. |
| 5,672,697 A | 9/1997 | Buhr et al. |
| 5,696,277 A | 12/1997 | Hostetler et al. |
| 5,717,095 A | 2/1998 | Arimilli et al. |
| 5,744,461 A | 4/1998 | Hostetler et al. |
| 5,744,592 A | 4/1998 | Hostetler et al. |
| 5,756,711 A | 5/1998 | Zilch et al. |
| 5,760,013 A | 6/1998 | Hwu et al. |
| 5,770,584 A | 6/1998 | Kucera et al. |
| 5,780,617 A | 7/1998 | van den Bosch et al. |
| 5,792,756 A | 8/1998 | Starrett, Jr. et al. |
| 5,798,340 A | 8/1998 | Bischofberger et al. |
| 5,817,638 A | 10/1998 | Hostetler |
| 5,827,831 A | 10/1998 | Hostetler et al. |
| 5,840,716 A | 11/1998 | Ubasawa et al. |
| 5,854,228 A | 12/1998 | Webb, II et al. |
| 5,856,314 A | 1/1999 | Kaas et al. |
| 5,869,468 A | 2/1999 | Freeman |
| 5,877,166 A | 3/1999 | Reist et al. |
| 5,885,973 A | 3/1999 | Papapoulos et al. |
| 5,886,179 A | 3/1999 | Arimilli et al. |
| 5,922,695 A | 7/1999 | Arimilli et al. |
| 5,922,696 A | 7/1999 | Casara et al. |
| 5,935,946 A | 8/1999 | Munger, Jr. et al. |
| 5,962,437 A | 10/1999 | Kucera et al. |
| 5,977,061 A | 11/1999 | Holy et al. |
| 5,977,089 A | 11/1999 | Arimilli et al. |
| 6,002,029 A | 12/1999 | Hostetler et al. |
| 6,030,960 A | 2/2000 | Morris-Natschke et al. |
| 6,043,230 A | 3/2000 | Arimilli et al. |
| 6,069,249 A | 5/2000 | Arimilli et al. |
| 6,194,388 B1 | 2/2001 | Krieg et al. |
| 6,207,646 B1 | 3/2001 | Krieg et al. |
| 6,218,371 B1 | 4/2001 | Krieg et al. |
| 6,225,292 B1 | 5/2001 | Raz et al. |
| 6,239,116 B1 | 5/2001 | Krieg et al. |
| 6,252,060 B1 | 6/2001 | Hostetler |
| 6,448,392 B1 | 9/2002 | Hostetler et al. |
| 6,562,798 B1 | 5/2003 | Schwartz |
| 6,589,940 B1 | 7/2003 | Raz et al. |
| 6,605,602 B1 | 8/2003 | Vats |
| 6,635,472 B1 | 10/2003 | Lauermann |
| RE38,333 E | 11/2003 | Arimilli et al. |
| 6,670,341 B1 | 12/2003 | Kucera et al. |
| 6,716,825 B2 | 4/2004 | Hostetler et al. |
| 6,818,629 B2 | 11/2004 | Peterson et al. |
| 7,026,469 B2 | 4/2006 | Kucera et al. |
| 7,034,014 B2 | 4/2006 | Hostetler et al. |
| 7,094,772 B2 | 8/2006 | Hostetler et al. |
| 7,098,197 B2 | 8/2006 | Hostetler et al. |
| 7,288,265 B1 | 10/2007 | Rolf |
| 7,390,791 B2 | 6/2008 | Becker et al. |
| 7,452,898 B2 | 11/2008 | Hostetler et al. |
| 7,652,001 B2 | 1/2010 | Hostetler et al. |
| 7,749,983 B2 | 7/2010 | Hostetler et al. |
| 7,790,703 B2 | 9/2010 | Hostetler et al. |
| 2003/0211072 A1 | 11/2003 | Carreno-Gomez et al. |
| 2004/0019232 A1 | 1/2004 | Hostetler et al. |
| 2004/0022873 A1 | 2/2004 | Guilford et al. |
| 2004/0071757 A1 | 4/2004 | Rolf |
| 2004/0161398 A1 | 8/2004 | Kucera et al. |
| 2004/0224917 A1 | 11/2004 | Dahl et al. |
| 2004/0259845 A1 | 12/2004 | Kucera et al. |
| 2005/0187192 A1 | 8/2005 | Fleming et al. |
| 2005/0261237 A1 | 11/2005 | Boojamra et al. |
| 2005/0267217 A1 | 12/2005 | Baron et al. |
| 2006/0128692 A1 | 6/2006 | Chen et al. |
| 2006/0263355 A1 | 11/2006 | Quan et al. |
| 2007/0003516 A1 | 1/2007 | Almond et al. |
| 2007/0003608 A1 | 1/2007 | Almond et al. |
| 2007/0026056 A1 | 2/2007 | Rolf |
| 2008/0009462 A1 | 1/2008 | Hostetler et al. |
| 2008/0020018 A1 | 1/2008 | Moodley et al. |
| 2008/0161324 A1 | 7/2008 | Johansen et al. |
| 2009/0017448 A1 | 1/2009 | Toth et al. |
| 2009/0087451 A1 | 4/2009 | Buller |
| 2009/0111774 A1 | 4/2009 | Tokars et al. |
| 2010/0173870 A1 | 7/2010 | Hostetler et al. |
| 2013/0035313 A1 | 2/2013 | Almond et al. |

FOREIGN PATENT DOCUMENTS

| | | |
|---|---|---|
| EP | 0186405 A2 | 7/1986 |
| EP | 0253412 A2 | 1/1988 |
| EP | 0632048 A1 | 1/1995 |
| EP | 0753523 A1 | 1/1997 |
| EP | 0897709 A1 | 2/1999 |
| EP | 1438962 A1 | 7/2004 |
| EP | 1914237 A2 | 4/2008 |
| GB | 1280788 A | 7/1972 |
| JP | 61152694 A | 7/1986 |
| JP | 10029998 A | 2/1998 |
| WO | WO-9105558 A1 | 5/1991 |
| WO | WO-9109602 A2 | 7/1991 |
| WO | WO-9520980 A1 | 8/1995 |
| WO | WO 96/33200 A1 | 10/1996 |
| WO | WO-9640088 A1 | 12/1996 |
| WO | WO-9818810 A1 | 5/1998 |
| WO | WO-9838202 A1 | 9/1998 |
| WO | WO-9908685 A1 | 2/1999 |
| WO | WO-0004032 A1 | 1/2000 |
| WO | WO-0006588 B1 | 4/2000 |
| WO | WO-0037477 A1 | 6/2000 |
| WO | WO-0112223 A3 | 9/2001 |
| WO | WO-0021556 A9 | 10/2001 |
| WO | WO-0122990 A3 | 10/2001 |
| WO | WO-0139724 A3 | 10/2001 |
| WO | WO-03030934 A2 | 4/2003 |
| WO | WO-03049746 A2 | 6/2003 |
| WO | WO-2004062600 A2 | 7/2004 |
| WO | WO-2004112718 A3 | 4/2005 |
| WO | WO2005/087788 | 9/2005 |
| WO | WO-2005121378 A2 | 12/2005 |
| WO | WO-2006017044 A2 | 2/2006 |
| WO | WO-2006066074 A2 | 6/2006 |

(56) References Cited

FOREIGN PATENT DOCUMENTS

| WO | WO-2006076015 A2 | 7/2006 |
|---|---|---|
| WO | WO-2006110655 A2 | 10/2006 |
| WO | WO-2006110656 A2 | 10/2006 |
| WO | WO2006/130217 | 12/2006 |
| WO | WO-0122972 A9 | 12/2006 |
| WO | WO-2007130783 A2 | 11/2007 |
| WO | WO 2008/007392 A3 | 1/2008 |
| WO | WO-2008033466 A2 | 3/2008 |
| WO | WO-2008118013 A2 | 10/2008 |
| WO | WO-2008133966 A1 | 11/2008 |
| WO | WO-2008133982 A2 | 11/2008 |
| WO | WO-2008144743 A1 | 11/2008 |
| WO | WO-2009082818 A1 | 7/2009 |
| WO | WO-2009082819 A1 | 7/2009 |
| WO | WO-2011011519 A1 | 1/2011 |
| WO | WO-2011017253 A1 | 2/2011 |
| WO | WO-2011053812 A1 | 5/2011 |

OTHER PUBLICATIONS

Gallant et al. "Tenofovir disoproxil fumarate (Viread} for the treatment of HIV infection," Expert Review of Anti-Infective Therapy, 2003, vol. 1, No. 3, pp. 415-422.*

Collier "Efficacy of combination antiviral therapy, Advance in Experimental Medicine and Biology," 1996, vol. 394, pp. 355-372.*

Borroto-Esoda, K. et al., "In vitro evaluation of the anti-HIV activity and metabolic interactions of tenofovir and emtricitabine, "Antiviral Therapy, vol. 11, No. 3, Jan. 1, 2006, pp. 377-384.

Cihlar, T. et al., "Design and Profiling of GS-9148, a Novel Nucloetide Analog Active against Nucleoside-Resistant Variants of Human Immunodeficiency Virus Type 1, and Its Orally Bioavailable Phosphonoamidate Prodrug, GS-9131, " Antimicrobial Agents and Chemotherapy, vol. 52, Feb. 2008, p. 655-665.

Delaney IV, W.E. et al., "Combinations of Adefovir with Nucleoside Analogs Produce Additive Antiviral Effects against Hepatitis B Virus In Vitro," Antimicrobrobial Agents and Chemotherapy, vol. 48, Oct. 2004, p. 3702-3710.

Franchetti, P. et al., "Inhibition of HIV-1 Replication in Macrophages by Red Blood Cell-Mediated Delivery of a Heterodinucleotide of Lamivudine and Tenofovir," Nucleosides, Nucleotides, and Nucleic Acids, 26:953-957, 2007.

Fung, H.B. et al., "Tenofovir Disoproxil Fumarate: A Nucleotide Reverse Transcriptase Inhibitor for the Treatment of HIV Infection," Clinical Therapeutics/vol. 24, No. 10, 2002.

Lyseng-Williamson, K. A. et al., "Tenofovir Disoproxil Fumarate a Review of its Use in the Management of HIV infection,"Drugs, 2005, 65 (3), pp: 413-432.

Myrick, F. et al., "The Trible Combination of Tenofovir, Emtricitabine and Efavirenz Shows Synergistic Anti-HIV-1 Activity In Vitro," Program and Abstracts/Antiviral Research, vol. 74, No. 3, Mar. 27, 2007, p. A61.

Painter, G.R. et al., "Evaluation of Hexadecyloxypropyl-9-R-[2-(Phosphonomethoxy) Propyl]-Adenine, CMX157, as a Potential Teatment for Human Immunodeficiency Virus Type 1 and Hepatitis B Virus Infections, "Antimicrobial Agents and Chemotherapy, vol. 51, Oct. 2007, p. 3505-3509.

Ray, A.S. "Lack of a metabolic and antiviral drug interaction between tenofovir, abacavir and lamivudine,"Antiviral Therapy, vol. 10, No. 3, (2005), pp. 451-457.

International Search Report for corresponding PCT application No. PCT/US2009/000447, mail date Jul. 29, 2009.

"Creating Orally Available Medicines from Bioactive Molecules." Presentation at BIG 2004 Annual International Convention. (Jun. 7, 2004).

Aldern et al. "Increased Antiviral Activity of 1-O-Hexadecyloxypropyl-[2-14C]Cidofovir in MRC-5 Human Lung Fibroblasts is Explained by Unique Cellular Uptake and Metabolism." Mol. Pharmacol. 63.3(2003):678-681.

Andrei et al. "Activities of Various Compounds against Murine and Primate Polyomaviruses." Antimicrob. Agents Chemother. 41.3(1997):587-593.

Annaert et al. "In Vitro, Ex Vivo, and In Situ Intestinal Absorption Characteristics of the Antiviral Ester Prodrug Adefovir Dipivoxil." J. Pharm. Sci. 89.8(2000):1054-1062.

Balzarini et al. "Antiretrovirus Activity of a Novel Class of Acyclic Pyrimidine Nucleoside Phosphonates." Antimicrob. Agents Chemother. 45.7(2002):2185-2193.

Bartlett et al. "Phase I Trial of Doxorubicin with Cyclosporine as a Modulator of Multidrug Resistance."J. Clin. Oncol. 12.4(1994):835-842.

Beadle et al. "Alkoxyalkyl Esters of Cidofovir and Cyclic Cidofovir Exhibit Mutiple-Log Enhancement of Antiviral Activity Against Cytomegalovirus and Herpes Virus Replication In Vitro." Antimicrob Agents Chemother. 46.8(2002):2381-2386.

Berge et al. "Pharmaceutical Salts." J. Pharmaceutical Sci. 66.1(1977):1-19.

Bidanset et al. "Oral Activity of Ether Lipid Ester Prodrugs of Cidofovir against Experimental Human Cytomegalovirus Infection." J. Infect. Dis. 190.3(2004):499-503.

Biron. "Antiviral Drugs for Cytomegalovirus Diseases." Antiviral Res. 71(2006):154-163.

Blasco et al. "Extracellular Vaccinia Virus Formation and Cell-to-Cell Virus Transmission are Prevented by Deletion of the Gene Encoding the 37,000-Dalton Outer Envelope Protein." J. Virol. 65.11(1991):5910-5920.

Bray et al. "Antiviral Prophylaxis of Smallpox." J. Antimicrob. Chemother. 54.1(2004):1-5.

Buller et al. "Efficacy of Oral Active Ether Lipid Analogs of Cidofovir in a Lethal Mousepox Model." Virol. 318.2(2004):474-481.

Buller et al. "Efficacy of Smallpox Vaccination in the Presence of Antiviral Drugs, Cidofovir, and Hexadecyoxypropylcidofovir." Antiviral Res. 65.3(2005):A80. (Abstract #72).

Ciesla et al. "Esterification of Cidofovir with Alkoxyalkanols Increases Oral Bioavailability and Diminishes Drug Accumulation in Kidney." Antiviral Res. 59.3(2003):163-171.

Connelly et al. "Mechanism of Uptake of the Phosphonate Analog (S)-1-(3-hydroxy-2-phosphonylmethoxy-propyl)Cytosine (HPMPC) in Vero Cells." Biochem. Pharma. 46.6(1993):1053-1057.

Dal Pozzo et al. "In Vitro Evaluation of the Anti-orf Virus Activity of Alkoxyalkyl Esters of CDV, cCDV and (S)-HPMPA." Antiviral Res. 75(2007):52-57.

De Clercq et al. "Therapeutic Potential of Nucleoside/Nucleotide Analogues Against Poxvirus Infections." Rev. Med. Virol. 14.5(2004):289-300.

De Clercq. "Antiviral Drugs in Current Clinical Use." J. Virol. 30.2(2004):115-133.

De Clercq. "Clinical Potential of the Acyclic Nucleoside Phosphonates Cidofovir, Adefovir, and Tenofovir in Treatment of DNA Virus and Retrovirus Infections." Clin. Microbiol. Rev. 16.4(2003):569-596.

De Clercq. "The Acyclic Nucleoside Phosphonates from Inception to Clinical Use: Historical Perspective." Antiviral Res. 75(2007):1-13.

De Clercq. "Vaccinia Virus Inhibitors as a Paradigm for the Chemotherapy of Poxvirus Infections." Clin. Microbiol. Rev. 14.2(2001):382-397.

Denes et al. "Main Adult Herpes Virus Infections of the CNS." Anti-Infective Therapy. 3.4(2005):663-678.

Fardis et al. "Case Study: Tenofovir Disoproxil Fumarate: An Oral Prodrug of Tenofovir." Volume V: Prodrugs: Challenges and Rewards Part 1. Biotechnology, Pharmaceutical Aspects. 5.20(2007):649-657.

Fisher et al. "Phase I Trial of Etoposide with the Cyclosporine SDZ PSC 833, a Modulator of Multidrug Resistance (MDR)." Proc. Am Soc. Clin. Oncol. 12(1994):143 (Abstract #368).

Gauvry et al. "Dealkylation of Dialkyl Phosphonates with Boron Tribromide." Synthesis. 4(2001):553-554.

Hammond et al. "Alkylglycerol Prodrugs of Phosphonoformate are Potent In Vitro Inhibitors of Nucleoside-Resistant Human Immunodeficiency Virus Type 1 and Select for Resistance Mutations

(56) References Cited

OTHER PUBLICATIONS that Suppress Zidovudine Resistance." *Antimicrob. Agents Chemother.* 45.6(2001):1621-1628.
Hartline et al. "Ether Lipid-Ester Prodrugs of Acyclic Nucleoside Phosphonates: Activity Against Adenovirus Replication In Vitro." *J. Infect. Dis.* 191.3(2005):396-399.
Held et al. "Treatment of BK Virus-Associated Hemorrhagic Cystitis and Simultaneous CMV Reactivation with Cidofovir." *Bone Marrow Transplant.* 26(2000):347-350.
Hillenkamp et al. "Topical Treatment of Acute Adenoviral Keratoconjunctivitis With 0.2% Cidofovir and 1% Cyclosporine." *Arch. Ophthalmol.* 119.10(2001):1487-1491.
Hockova et al. "5-Substituted-2,4-diamino-642-(phosphonomethoxy)ethoxy]pyrimidines-Acyclic Nucleoside Phosphonate Analogues with Antiviral Activity." *J. Med. Chem.* 46.23(2003):50645073.
Holy et al. "6-[2-(Phosphonomethoxy)alkoxy]pyrimidines With Antiviral Activity." *J. Med. Chem.* 45.9(2002):1918-1929.
Holy et al. "Structure-Antiviral Activity Relationship in the Series of Pyrimidine and Purine N[2(2-Phosphonomethoxy)ethyl] Nucleotide Analogues." *J. Med. Chem.* 42.12(1999):2064-2086.
Holy. "Phosphonomethoxyalkyl Analogs of Nucleotides." *Curr. Pharma Des.* 9.31(2003):2567-2592.
Holy. "Simple Method for Cleavage of Phosphonic Acid Diesters to Monoesters." *Synthesis.* 4(1998):381-385.
Hostetler et al. "Enhanced Antiproliferative Effects of Alkozyalkyl Esters of Cidofovir in Human Cervical Cancers Cells in vitro." *Mol. Cancer Ther.* 5.1(2005):156-159.
Hostetler. "Alkoxyalkyl Prodrugs of Acyclic Nucleoside Phosphonates Enchance Oral Antiviral Activity and Reduce Toxicity: Current State of the Art." *Antiviral Research.* 82.2(2009):A84-A98.
Huggins et al. "Cidofovir Treatment of Variola (Smallpox) in the Hemorrhagic Smallpox Primate Model and the IV Monkeypox Primate Model." *Antiviral Res.* 57.3(2003):A78. (Abstract #127).
Huggins et al. "Orally Active Ether Lipid Prodrugs of Cidofovir for the Treatment of Smallpox." *Antiviral Res.* 53(2002):A66. (Abstract #104).
Huggins et al. "Successful Cidofovir Treatment of Smallpox-Like Disease in Variola and Monkeypox Primate Models." *Antiviral Res.* 62.2(2004):A57-A58. (Abstract #76).
Jacobson. "Treatment of Cytomegalovirus Retinitis in Patients with the Acquired Immunodeficiency Syndrome." *Drug Ther.* 337(1997):105-114.
Jasko et al. "A New Approach to Synthesis of 5'-)-phosphonomethyl Derivatives of Nucleosides and Their Analogues." *Bioorganicheskaya Khimiya.* 20.1(1994):50-54. (English Abstract Only).
Josephson et al. "Polyomavirus-Associated Nephropathy: Update on Antiviral Strategies." *Transpl. Infect. Dis.* 8(2006):95-101.
Keith et al. "Evaluation of Nucleoside Phosphonates and Their Analogs and Prodrugs for Inhibition of Orthopoxvirus Replication." *Antimicrob Agents Chemother.* 47.7(2003):2193-2198.
Keith et al. "Inhibitory Activity of Alkoxyalkyl and Alkyl Esters of Cidofovir and Cyclic Cidofovir Against Orthopoxvirus Replication In Vitro." *Antimicrob. Agents Chemother.* 48.5(2004):1869-1871.
Kern et al. "Enhanced Inhibition of Orthopoxvirus Replication In Vitro by Alkoxyalkyl Esters of Cidofovir and Cyclic Cidofovir." *Antimicrob. Agents Chemother.* 46.4(2002):991-995.
Kern et al. "Oral Treatment of Murine Cytomegalovirus Infections with Ether Lipid Esters of Cidofovir." *Antimicrob Agents Chemother.* 48.9(2004):3516-3522.
Kini et al. "Alkoxy Propane Prodrugs of Foscarnet: Effect of Alkyl Chain Length on in Vitro Antiviral Activity in Cells Infected with HIV-1, HSV-1 and HCMV." *Antiviral Res.* 36.1(1997):43-53.
Kornbluth et al. "Mutations in the E9L Polymerase Gene of Cidofovir-Resistant Vaccinia Virus Strain WR are Associated with the Drug Resistance Phenotype." *Antimicrob. Agents Chemother.* 50.12(2006):4038-4043.
Lebeau et al. "Activities of Alkoxyalkyl Esters of Cidofovir (CDV), Cyclic CDV, and (S)-9-(3- Hydroxy-2- Phosphonylmethoxypropyl)Adenine Against Orthopoxviruses in Cell Monolayers and in Organotypic Cultures." *Antimicrob. Agents Chemother.* 50.7(2006):2525-2529.
Lu et al. "Intraocular Properties of Hexadecyloxypropyl-Cyclic-Cidofovir in Guinea Pigs." *J. Ocul. Pharmacol. Ther.* 21.3(2005):205-209.
Niemi et al. "Bisphosphonate Prodrugs: Synthesis and in Vitro Evaluation of Novel Acyloxyalkyl Esters of Clodronic Acid." *J. Med. Chem.* 42.24(1999):5053-5058.
Painter et al. "Biochemical and Mechanistic Basis for the Activity of Nucleoside Analogue Inhibitors of HIV Reverse Transcriptase." *Curr. Topics Med. Chem.* 4.10(2004):1035-1044.
Painter et al. "Design and Development of Oral Drugs for the Prophylaxis and Treatment of Smallpox Infection." *Trends Biotechnol.* 22.8(2004):423-427.
Parker et al. "Efficacy of Therapeutic Intervention with an Oral Ether-Lipid Analogue of Cidofovir (CMX001) in a Lethal Mousepox Model." *Antiviral Res.* 77.1(2008):39-49.
Portilla et al. "Progressive Multifocal Leukoencephalopathy Treated with Cidofovir in HIV-Infected Patients Receiving Highly Active Anti-Retroviral Therapy." *J. Infect.* 41(2000):182-184.
Quenelle et al. "Oral Treatment of Cowpox and Vaccinia Virus Infections in Mice with Ether Lipid Esters of Cidofovir." *Antimicrob. Agents Chemother.* 48.2(2004):404-412.
Quenelle et al. "Oral Treatment of Cowpox and Vaccinia Virus Infections in Mice with Ether Lipid Esters of Cidofovir." *Antimicrob. Agents Chemother.* 48.2(2004):404-412. Erratum in: *Antimicrob. Agents Chemother.* 48.5(2004):1919.
Quenelle et al. "Synergistic Efficacy of the Combination of ST-246 with CMX001 Against Orthopoxviruses." *Antimicrob. Agents Chemother.* 51.11(2007):4118-4127.
Randhawa et al. "Ether Lipids Ester Derivatives of Cidofovir Inhibit Polyomavirus BK Replication In Vitro." *Antimicrob. Agents Chemother.* 50.4(2006):1564-1566.
Remichkova et al. "Synergistic Combination Effect of Cidofovir and Idoxuridine on Vaccinia Virus Replication." *Antiviral Res.* 65.3(2005):A80-A81. (Abstract #74).
Rogers. "A General Synthesis of Phosphonic Acid Dichlorides Using Oxalyl Chloride and DMF Catalysis." *Tetrahed. Lett.* 33.49(1992):7473-7474.
Saady et al. "Direct Esterification of Phosphonic Acid Salts Using the Mitsunobu Reaction." *Synlett.* 6(1995):643-644.
Smee et al. "A Review of Compounds Exhibiting Anti-Orthopoxvirus Activity in Animal Models." *Antiviral Res.* 57.1-2(2003):41-52.
Smee et al. "Characterization and Treatment of Cidofovir-Resistant Vaccinia (WR Strain) Virus Infections in Cell Culture and in Mice." *Antiviral Chem. Chemother.* 16.3(2005):203-211.
Smee et al. "Effects of Four Antiviral Substances on Lethal Vaccinia Virus (IHD Strain) Respiratory Infections in Mice." *Int. J. Antimicrob. Agents.* 23.5(2004):430-437.
Toth et al. "Hexadcyloxypropyl-Cidofovir, CMX001, Prevents Adenovirus-Induced Mortality in a Permissive, Immunosuppressed Animal Model." *PNAS.* 105.20(2008):7293-7297.
Wan et al. "Alkoxyalkyl Esters of Cidofovir and Cyclic Cidofovir: Effects of Alkyl Chain Length, Unsaturation, and Substitution on the in vitro Antiviral Activity in Cells Infected with HSV-1 and HCMV." *224th ACS National Meeting.* Boston, MA. Aug. 18-22, 2002. (Abstract #MEDI-30).
Wan et al. "Comparison of the Antiviral Activities of Alkoxyalkyl and Alkyl Esters of Cidofovir Against Human and Murine Cytomegalovirus Replication In Vitro." *Antimicrob. Agents Chemother.* 49.2(2005):656-662.
Wawzonek et al. "Preparation of Long Chain Alkyl Hydroperoxides." *J. Org. Chem.* 25.4(1960):621-623.
Williams-Aziz et al. "Comparative Activities of Lipid Esters of Cidofovir and Cyclic Cidofovir Against Replication of Herpesviruses in Vitro." *Antimicrob. Agents Chemother.* 49.9(2005):3724-3733.
Yang et al. "An Orally Bioavailable Antipoxvirus Compound (ST-246) Inhibits Extracellular Virus Formation and Protects Mice from Lethal Orthopoxvirus Challenge." *J. Virol.* 79.20(2005):13139-13149.

(56) References Cited

OTHER PUBLICATIONS

Zanger et al. "Structure-Activity Relationship and Drug Design." *Remington's Pharmaceutical Sciences*. (1980):420-435.

Kearney et al. "Tenofovir Disoproxil Fumarate: Clinical Pharmacology and Pharmacokinetics." *Clin. Pharmacokinet*. 43.9(2004):595-612.

Madeddu et al. "Renal Toxicity in HIV-Infected Patients Receiving HAART Including Tenofovir." *Infez. Med*. 14.3(2006):125-134. (Italian Original and English Abstract).

Michaud et al. "The Dual Role of Pharmacogenetics in HIV Treatment: Mutations and Polymorphisms Regulating Antiretroviral Drug Resistance and Disposition." *Pharm. Rev*. 64.3(2012):803-833.

Wallot et al. "Disseminated Adenovirus Infection with Respiratory Failure in Pediatric Liver Transplant Recipients: Impact of Intravenous Cidofovir and Inhaled Nitric Oxide." *Pediatr. Transplantation*. 10(2006):121-127.

Zimmermann et al. "Tenofovir-Associated Acute and Chronic Kidney Disease: A Case of Multiple Drug Interactions." *Clin. Infect. Dis*. 42(2006):283-290.

Hostetler, K.Y. et al., "Alkoxyalkyl Esters of (S)-9-[3-Hydroxy-2-(Phosphonomethoxy)Propyl]Adenine Are Potent Inhibitors of the Replication of Wild-Type and Drug-Resistant Human Immunodeficiency Virus Type 1 In Vitro", *Antimicrobial Agents and Chemotherapy*, 50(8):2875-2879 (2006).

Hostetler, K., "In vitro and in vivo evaluation of hexadecyloxypropyl-9-R-[2-(phosphono-methoxy) propyl]adenine as a potential treatment of HIV-1 infection", *Global Antiviral Journal*, Abstract 84, 2(2):96-97 (2006).

\* cited by examiner

METHODS OF TREATING VIRAL INFECTIONS

RELATED APPLICATIONS

This application is a 35 U.S.C. §371 national phase application of PCT Application PCT/US2009/000447, filed Jan. 23, 2009, and published in English on Jul. 30, 2009, as International Publication No. WO 2009/094190, and which claims the benefit under 35 U.S.C. §119(e) of U.S. Provisional Patent Application Ser. No. 61/023,633, filed Jan. 25, 2008, and U.S. Provisional Application Ser. No. 61/101,810, filed Oct. 1, 2008, the disclosure of which is incorporated herein by reference in their entireties.

BACKGROUND OF THE INVENTION

Human immunodeficiency virus type 1 (HIV-1) encodes three enzymes which are required for viral replication: reverse transcriptase, protease, and integrase. Combination therapy with protease inhibitors and reverse transcriptase inhibitors has a long record of effectively treating HIV and integrase inhibitors are starting to make significant contributions (See Palella, et al, N. Engl. J. Med., 338, 853-860 (1998); Richman, Nature, 410, 995-1001(2001)). However, therapy frequently fails due to the development of drug resistance, non-compliance with complicated dosing regimens, pharmacokinetic interactions, toxicity, and/or lack of potency. Therefore, there is a continuing need for new therapies that are active against mutant HIV strains, have fewer side effects, and permit simpler dosing schedules.

SUMMARY OF THE INVENTION

A first aspect of the invention is, in a method of treating a subject for human immunodeficiency virus (HIV) and/or hepatitis B virus (HBV) infection (in some embodiments thereof, said subject has not previously been administered an antiviral active agent for said HIV or HBV infection), the method including: administering said subject an antiviral compound of Formula (I)-(III) and (V)-(X) described herein, or a pharmaceutically acceptable salt, a stereoisomer, a diastereomer, an enantiomer or racemate thereof, in an amount effective to treat said viral infection and substantially inhibit the development of resistance to antiviral compounds in said subject.

A further aspect of the invention is, in a method of treating a subject for human immunodeficiency virus (HIV) and/or hepatitis B virus (HBV) infection, where said subject has developed resistance, or a toxic response, to at least one antiviral compound in response to prior administration of at least one antiviral compound to said subject for said HIV or HBV infection, the method including: administering said subject an antiviral compound of Formula (I)-(III) and (V)-(X) described herein, or a pharmaceutically acceptable salt, or a stereoisomer, a diastereomer, an enantiomer or racemate thereof, in an amount effective to treat said viral infection and inhibit the further development of resistance to antiviral compounds in said subject.

The aforesaid methods may further include concurrently administering said subject one or more additional antiviral active agents with said an antiviral compound.

In some embodiments of the foregoing, the subject is immunocompromised (e.g., by said virus).

In some embodiments of the foregoing, the virus is HBV (and in some embodiments thereof, the subject is afflicted with fulminant hepatitis or fulminant hepatic failure).

In some embodiments of the foregoing, the subject is infected with both HBV and HIV, said antiviral compound is administered in an amount effective to treat both said HBV and HIV.

In some embodiments of the foregoing, the subject is in utero and said active compound is administered to the mother carrying said subject in utero.

A further aspect of the invention is the use of an antiviral compound of Formula (I)-(III) and (V)-(X) described herein as described herein for carrying out a method as described herein, and/or for the preparation of a medicament for carrying out a method as described herein.

A further aspect of the invention is a pharmaceutical composition comprising: (a) an antiviral compound of Formula (I)-(III) and (V)-(X) described herein, or pharmaceutically acceptable salt, or a stereoisomer, a diastereomer, an enantiomer or racemate thereof, (b) one or more additional antiviral active agents (e.g., an anti HIV or an anti HBV antiviral compound); and (c) a pharmaceutically acceptable carrier.

Also described herein is the finding that active compounds described herein associate or bind directly to viruses such as HIV, making possible the delivery of the active compounds into cellular or tissue compartments (sometimes referred to as "privileged compartments") to which active compounds are not otherwise accessible, and making the active compounds useful as microbicides to inhibit the transmission (e.g., prophylactically) of viruses such as HIV. Compositions and devices for carrying out such methods, along with the use of active compounds as described herein for carrying out such methods, are also described.

In some embodiments, in the above methods, device, or compositions, the one or more additional antiviral agents can be selected from the group consisting of lamivudine, abacavir, zidovudine, stavudine, zalcitabine, didanosine, emtricitabine, tenofovir, delavirdine, efavirenz, etravirine, nevirapine, amprenavir, atazanavir, darunavir, indinavir, lopinavir, nelfinavir, ritonavir, saquinavir, tipranavir, maraviroc, enfuvirtide, and raltegravir.

DETAILED DESCRIPTION

Figure 1:
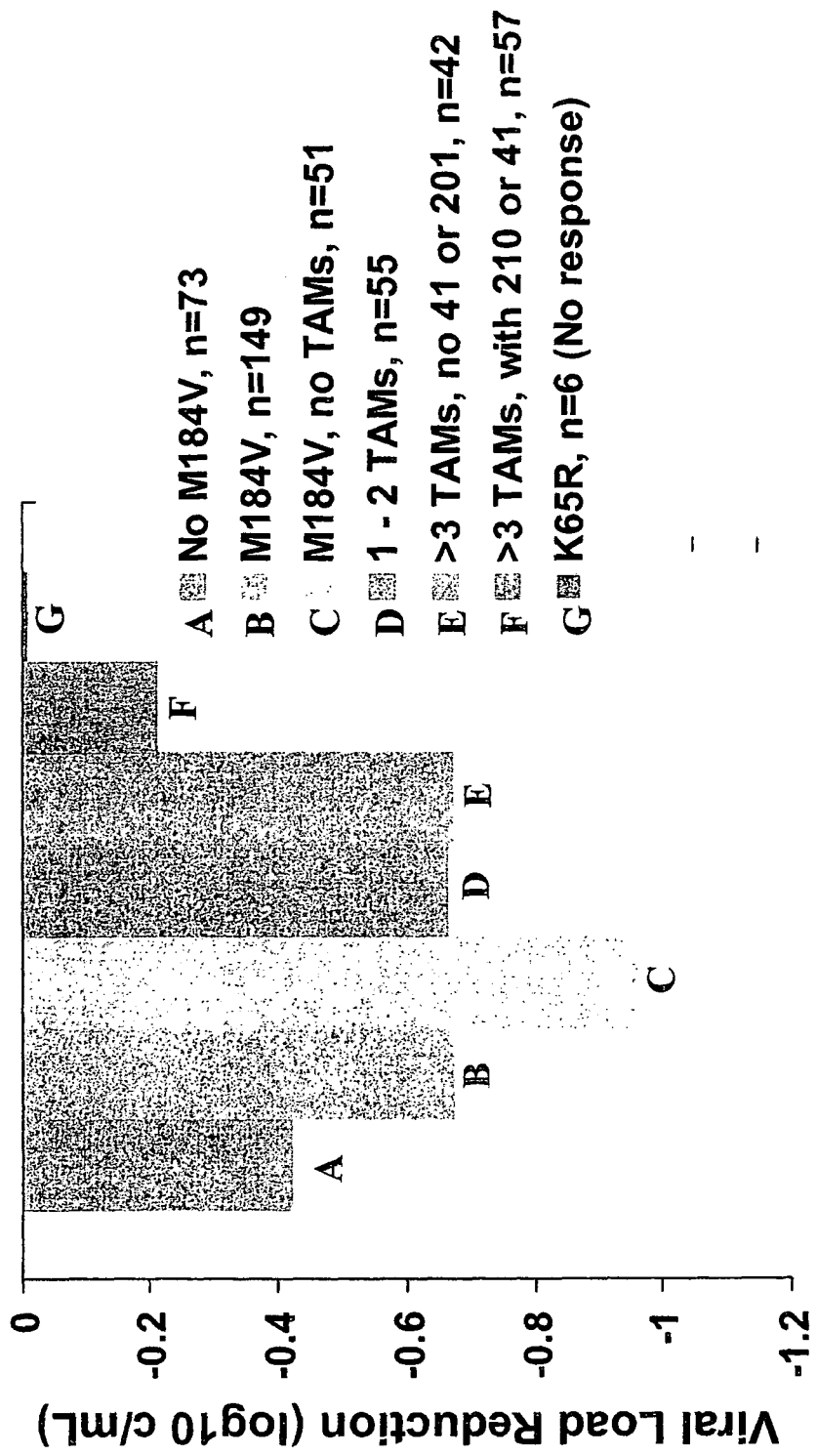
FIG. 1 shows for comparative purposes the virologic response to tenofovir in antiretroviral experienced patients at 24 weeks.

The foregoing and other aspects of the present invention will now be described in more detail with respect to the description and methodologies provided herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the embodiments of the invention and the appended claims, the singular forms "a", "an" and "the" are intended to include the plural forms as well, unless the context clearly indicates otherwise. Also, as used herein, "and/or" refers to and encompasses any and all possible combinations of one or more of the associated listed items. Furthermore, the term "about," as used herein when referring to a measurable value such as an amount of a compound, dose, time, temperature, and the like, is meant to encompass variations of 20%, 10%, 5%, 1%, 0.5%, or even 0.1% of the specified amount. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Unless otherwise defined, all terms, including technical and scientific terms used in the description, have the same meaning as commonly understood by one of ordinary skill in the art to which this invention belongs.

All patents, patent applications and publications referred to herein are incorporated by reference in their entirety. In case of a conflict in terminology, the present specification is controlling.

As used herein, "alkyl" refers to a straight or branched chain hydrocarbon containing from 1 to 30 carbon atoms. In some embodiments, the alkyl group contains 2 to 25, 2 to 24, 1 to 10, or 1 to 8 carbon atoms. In some embodiments the alkyl group contains 1 to 6 carbon atoms. In some embodiments, the alkyl group contains 1 to 4 carbon atoms. In still other embodiments, alkyl group contains 1-5 carbon atoms, and in yet other embodiments, alkyl group contain 1-4 or 1-3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. Additional examples or generally applicable substituents are illustrated by the specific embodiments shown in the Examples which are described herein.

As used herein, "alkenyl," refers to a straight or branched chain hydrocarbon containing from 2 to 30 carbons and containing at least one carbon-carbon double bond formed by the removal of two hydrogens. In some embodiments, the alkenyl group contains 2 to 25, 2 to 24, 2 to 10, 2 to 8 carbon atoms. In some embodiments, the alkenyl group contains 2 to 6 carbon atoms. In still other embodiments, alkenyl groups contain 2-5 carbon atoms, and in yet other embodiments alkenyl groups contain 2-4 or 2-3 carbon atoms. Representative examples of "alkenyl" include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl and the like. Additional examples or generally applicable substituents are illustrated by the specific embodiments shown in the Examples which are described herein.

As used herein, "alkynyl," refers to a straight or branched chain hydrocarbon group containing from 2 to 30 carbon atoms and containing at least one carbon-carbon triple bond. In some embodiments, the alkynyl group contains 2 to 25, 2 to 24, 2 to 10 or 2 to 8 carbon atoms. In some embodiments, the alkynyl group contains 2 to 6 carbon atoms. In still other embodiments, alkynyl groups contain 2-5 carbon atoms, and in yet other embodiments, alkynyl groups contain 2-4 or 2-3 carbon atoms. Representative examples of alkynyl include, but are not limited, to ethynyl, 1-propynyl, 2-propynyl, 3-butynyl, 2-pentynyl, 1-butynyl and the like. Additional examples or generally applicable substituents are illustrated by the specific embodiments shown in the Examples which are described herein.

As used herein, the term "alkoxy" refers to an alkyl group, as previously defined, attached to the parent molecular moiety through an oxygen atom. In some embodiments the alkyl group contains 1-30 carbon atoms. In other embodiment, the alkyl group contains 1-20, 1-10 or 1-5 carbon atoms. In some embodiments, the alkoxyl group contains 1 to 8 carbon atoms. In some embodiments, the alkoxyl group contains 1 to 6 carbon atoms. In some embodiments, the alkoxyl group contains 1 to 4 carbon atoms. In still other embodiments, alkoxyl group contains 1-5 carbon atoms, and in yet other embodiments, alkoxyl group contain 1-4 or 1-3 carbon atoms. Representative examples of alkoxyl include, but are not limited to, methoxy, ethoxy, propoxy, isopropoxy, n-butoxy, tert-butoxy, and n-pentoxy. Additional examples or generally applicable substituents are illustrated by the specific embodiments shown in the Examples which are described herein.

As used herein, "amino acid residue" refers to a compound consisting of a carbon atom which is bonded to a primary amino ($-NH_2$) group, a carboxylic acid ($-COOH$) group, a side chain, and a hydrogen atom. For example, the term "amino acid" includes, but is not limited to, Glycine, Alanine, Valine, Leucine, Isoleucine, Serine, Threonine, Aspartic acid and Glutamic acid. In the present invention, in Formula I or Ia, when $R_2$ is $-NR'H$ and R' is an amino acid residue, N is attached to the carbon atom as a side chain. Additionally, as used herein, "amino acid" also includes derivatives of amino acids such as esters, and amides, and salts, as well as other derivatives, including derivatives having pharmacoproperties upon metabolism to an active form. Additional examples or generally applicable substituents are illustrated by the specific embodiments shown in the Examples which are described herein.

As used herein, "cycloalkyl" refers to a monovalent saturated cyclic or bicyclic hydrocarbon group of 3-12 carbons derived from a cycloalkane by the removal of a single hydrogen atom. In some embodiments, cycloalkyl contains 3 to 8 carbon atoms. In some embodiments, cycloalkyl contains 3 to 6 carbon atoms. Cycloalkyl groups may be optionally substituted with alkyl, alkoxy, halo, or hydroxy substituents. Representative examples of cycloalkyl include, but are not limited to, are cyclopropyl, cyclobutyl, cyclopentyl, cyclohexyl, cycloheptyl, and cyclooctyl. Additional examples of generally applicable substituents are illustrated by the specific embodiments shown in the Examples that are described herein.

As used herein, "heteroalkyl," "heteroalkenyl" or "heteroalkynyl" refer to alkyl, alkenyl or alkynyl groups which contain one or more oxygen, sulfur, nitrogen, phosphorus or silicon atoms, e.g., in place of carbon atoms. In some embodiments, the heteroalkyl group contains 1-8 carbon atoms. In certain embodiments, the heteroalkenyl and heteralkynyl groups independently contain 2-8 carbon atoms. In still other embodiments, heteroalkyl, heteroalkenyl and heteralkynyl independently contain 2-5 carbon atoms, and in yet other embodiments, heteroalkyl, heteroalkenyl and heteralkynyl independently contain 2-4 or 2-3 carbon atoms.

The terms "heterocycle" or "heterocyclyl" represent a 3-, 4-, 5-, 6-, 7- or 8-membered saturated or unsaturated ring containing one, two or three heteroatoms independently selected from the group consisting of nitrogen, oxygen and sulfur. In some embodiments, the heterocycle contains 3, 4, 5, or 6 carbons. Representative heterocyclyl include, but not limited to, furanyl, thiophenyl, pyrrolyl, piperidinyl, 1,4-dioxanyl, morpholinyl, thiomorpholinyl, pyrolidinyl, oxazolyl, thiazolyl, imidazolyl, pyrazolyl, pyrazolinyl, isoxazolyl, isothiazolyl, and piperazinyl, As used herein, the term "halogen" refers to fluorine (F), chlorine (Cl), bromine (Br), or iodine (I) and the term "halo" refers to the halogen radicals: fluoro (—F), chloro (—Cl), bromo (—Br), and iodo (—I).

As used herein, the term "haloalkyl" refers to a straight or branched chain alkyl group as defined herein containing at least one carbon atoms substituted with at least one halo group, halo being as defined herein. In some embodiments, the haloalkyl contains 1 to 30 carbon atoms. In some embodiments, the halkalkyl contains 1 to 8 or 1 to 6 carbon atoms. In other embodiments, the haloalkyl contains 1 to 4 carbon atoms. Additional examples or generally applicable substituents are illustrated by the specific embodiments shown in the Examples which are described herein.

As used herein, the term "aryl" refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like. The term "aryl" is intended to include both substituted and unsubstituted aryl unless otherwise indicated. For example, an aryl may be substituted with one or more heteroatoms (e.g., oxygen, sulfur and/or nitrogen). Additional examples or generally applicable substituents are illustrated by the specific embodiments shown in the Examples which are described herein.

Subjects to be treated by the methods of the present invention are, in general, mammalian and primate subjects (e.g., human, monkey, ape, chimpanzee). Subjects may be male or female and may be of any age, including prenatal (i.e., in utero), neonatal, infant, juvenile, adolescent, adult, and geriatric subjects. Thus, in some cases the subjects may be pregnant female subjects. Treatment may be for any purpose, including the therapeutic treatment of previously infected subjects, as well as the prophylactic treatment of uninfected subjects (e.g., subjects identified as being at high risk for infection).

As used herein, "Human immunodeficiency virus" (or "HIV") as used herein is intended to include all subtypes thereof, including HIV subtypes A, B, C, D, E, F, G, and O, and HIV-2.

As used herein, "Hepatitis B virus" (or "HBV") as used herein is intended to include all subtypes (adw, adr, ayw, and ayr) and or genotypes (A, B, C, D, E, F, G, and H) thereof.

As used herein, "Multiple nucleoside resistant" or "multi-nucleoside resistant" as used herein refers to genotypic or phenotypic patterns which predict or indicate diminished efficacy for most or all nucleoside and nucleotide reverse transcriptase inhibitors. Genotypic examples include the Q151M complex, the T69SXX complex and multiple thymidine analog associated mutations. Phenotypic examples include patterns where few or no NRTIs test as "sensitive".

As used herein, "Toxic response" as used herein may be any deleterious toxic and/or undesired response to a treatment with an antiviral agent, including but not limited to nausea, vomiting, rash, diarrhea, nephrotoxicity, mitochondrial toxicity, etc. and combinations thereof.

As used herein, a "therapeutically effective amount" or "an amount effective" refers to an amount that will provide some alleviation, mitigation, and/or decrease in at least one clinical symptom in the subject. Those skilled in the art will appreciate that the therapeutic effects need not be complete or curative, as long as some benefit is provided to the subject.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

As used herein, the terms "treatment," "treat," and "treating" refer to reversing, alleviating, delaying the onset of, or inhibiting the progress of a disease or disorder as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Active compounds of the present invention may optionally be administered in conjunction with other active compounds and/or agents useful in the treatment of viral infections as described herein. The other compounds may optionally be administered concurrently. As used herein, the word "concurrently" means sufficiently close in time to produce a combined effect (that is, concurrently may be simultaneously, or it may be two or more events occurring within a short time period before or after each other).

A. Active Compounds.

Active compounds useful for carrying out the present invention are, in general, antiviral compounds of Formula I (or in some embodiments more particularly compounds of Formula Ia), or a pharmaceutically acceptable salt, or a stereoisomer, a diastereomer, an enantiomer or racemate thereof:

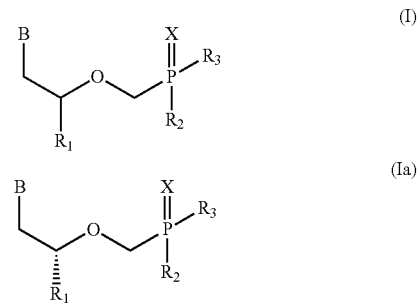

wherein:

B is a purine or pyrimidine base, including but not limited to: adenine, 6-chloropurine, xanthine, hypoxanthine, guanine, 8-bromoguanine, 8-chloroguanine, 8-aminoguanine, 8-hydrazinoguanine, 8-hydroxyguanine, 8-methylguanine, 8-thioguanine, 2-aminopurine, 2,6-diaminopurine, thymine, cytosine, 5-fluorocytosine, uracil; 5-bromouracil, 5-iodouracil, 5-ethyluracil, 5-ethynyluracil, 5-propynyluracil, 5-propyluracil, 5-vinyluracil, 5-bromovinyluracil;

$R_1$ is H, methyl, ethyl, —CH$_2$OH, —CH$_2$CH$_2$OH, —CH(OH)CH$_3$, or C$_{1-6}$ haloalkyl;

$R_2$ is fluoro, hydroxy, —OR$_{2a}$, —BH$_3$, C$_1$-C$_8$ alkyl, C$_{2-8}$ alkenyl, C$_{2-8}$ alkynyl, C$_{1-8}$ heteroalkyl, C$_{2-8}$ heteroalkenyl, C$_{2-8}$ heteroalkynyl, or —NR'H;

$R_{2a}$ is C$_{1-8}$ alkyl, C$_{2-8}$ alkenyl, C$_{2-8}$ alkynyl, C$_{1-8}$ heteroalkyl, C$_{2-8}$ heteroalkenyl, C$_{2-8}$ heteroalkynyl, —P(=O)(OH)$_2$, or —P(=O)(OH)OP(=O)(OH)$_2$, R' is $C_{1-8}$ alkyl, $C_{2-8}$ alkenyl, $C_{2-8}$ alkynyl, $C_{1-8}$ heteroalkyl, $C_{2-8}$ heteroalkenyl, $C_{2-8}$ heteroalkenyl, $C_{6-10}$ aryl, or an amino acid residue, $R_3$ is —$O(CH_2)_mO(CH_2)_nCH_3$, where m is from 2 to 5 (in some embodiments, 2 or 3) and n is from 11 to 21 (in some embodiments, 15 or 17); and X is selenium, sulphur, or oxygen (in some embodiments, oxygen)

Additional examples of base B include, but are not limited to, compounds of the general formula:

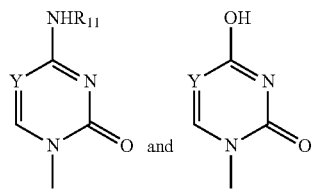

where:

Y is N or CX;

X is selected from the group consisting of H, halo, $C_{1-6}$ alkyl, $C_{2-6}$ alkenyl, $C_{2-6}$ alkynyl, CN, $CF_3$, $N_3$, $NO_2$, $C_{6-10}$ aryl, $C_{6-10}$ heteroaryl, and $COR_b$;

$R_b$ is selected from the group consisting of H, OH, SH, $C_{1-6}$ alkyl, $C_{1-6}$ aminoalkyl, $C_{1-6}$ alkoxy and $C_{1-6}$ thioalkyl; and $R_{11}$ is selected from the group consisting of H, $C_{1-6}$ alkyl, $C_{2-6}$ alkenyl, $C_{2-6}$ alkynyl, or $C_{6-10}$ aryl, and carbonyl substituted with a $C_{1-6}$ alkyl, $C_{2-6}$ alkenyl, $C_{2-6}$ alkynyl, or $C_{6-10}$ aryl. The example of B is further described in U.S. Pat. No. 6,583,149, which is incorporated by reference in its entirety.

Additional examples of base B include, but are not limited to, compounds of the general formula:

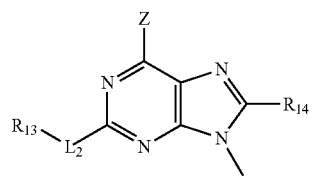

where:

Z is $NH_2$ or hydroxyl;

$L_2$ is a covalent bond (that is, is absent), —N(—$R_{15}$)—, N(—$R_{15}$)C(=O)—, —O—, —S—, —S(=O)—, or is —S(=O)$_2$—, $R_{13}$ is H, $C_{1-6}$ alkyl, $C_{1-6}$ heteroalkyl, $C_{2-6}$ alkenyl, $C_{6-10}$ aryl, $C_{7-16}$ arylalkyl, $C_{3-10}$ carbocyclyl, $C_{6-10}$ heterocyclyl, or $C_{7-16}$ heterocyclylalkyl;

$R_{14}$ is H, halo, hydroxy, alkoxy, —$O(CH_2)_xOC(=O)OR_{15}$, or $OC(=O)OR_{15}$, wherein X is 2 or 3 to 10, 15 or 20, and $R_{15}$ is H, $C_{1-6}$ alkyl, $C_{1-6}$ heteroalkyl, $C_{2-6}$ alkenyl, $C_{6-10}$ aryl, $C_{7-16}$ arylalkyl, $C_{3-10}$ cyclyl, $C_{6-10}$ heterocyclyl, or $C_{7-16}$ heterocyclylalkyl.

Additional examples of base B includes, but not limited to, compounds of the general formula:

$R_{16}$ and $R_{17}$ are independently selected from the group consisting of hydrogen, $C_{1-6}$ alkyl, or $C_{3-6}$ cycloalkyl, or N, $R_{16}$ and $R_{17}$ taken together to form $N_3$, $C_{3-8}$ heterocyclyl, wherein $C_{3-6}$ cycloalkyl and $C_{3-8}$ heterocyclyl can be optionally substituted with one or more $C_{1-5}$ alkyl.

Exemplary active compounds (tenofovir analogs) useful for carrying out the present invention include, but are not limited to:

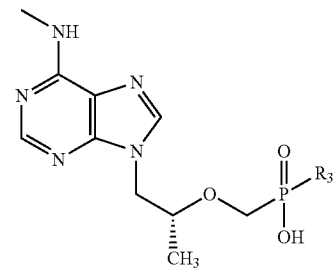

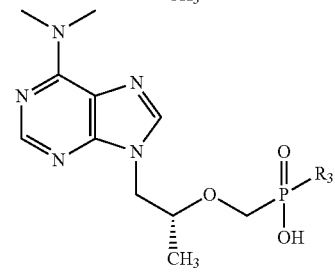

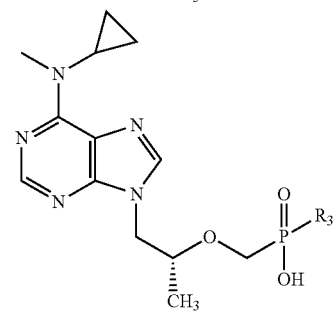

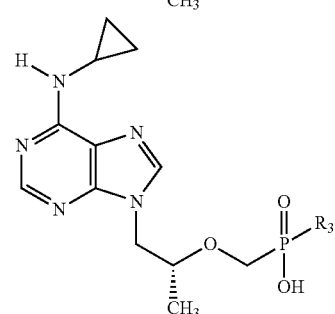

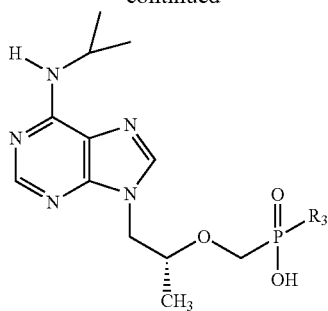

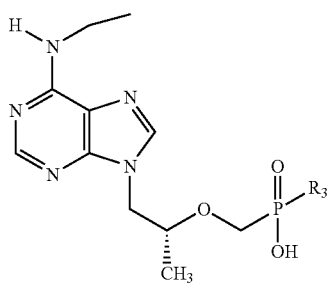

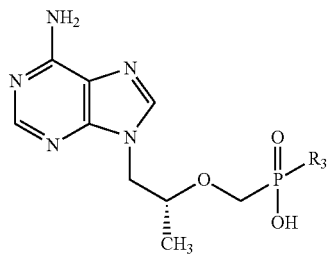

where R₃ is: O(CH₂)₂O(CH₂)₁₇CH₃ or O(CH₂)₃O(CH₂)₁₅CH₃

Additional examples of active compounds (tenofovir analogs) useful for carrying out the present invention include, but are not limited to:

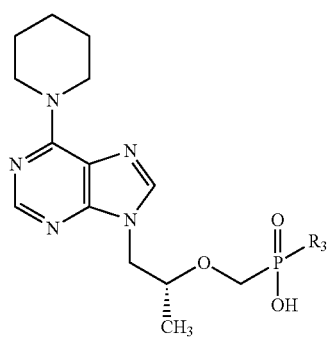

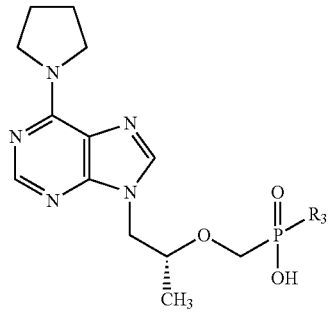

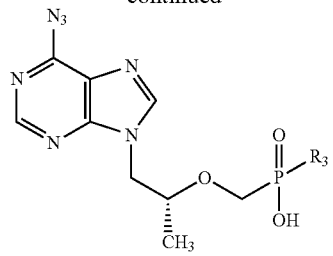

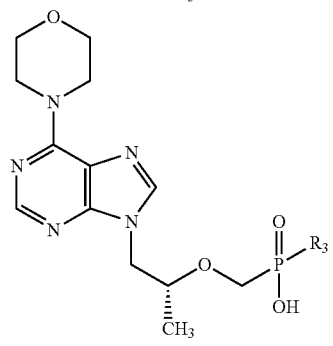

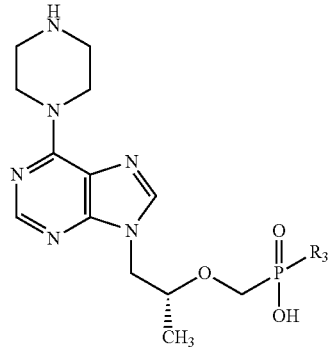

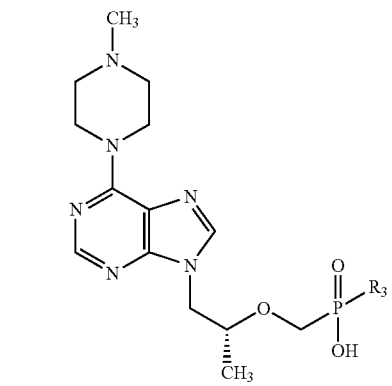

wherein R₃ is: O(CH₂)₂O(CH₂)₁₇CH₃ or O(CH₂)₃O(CH₂)₁₅CH₃

Additional examples of active compounds (adefovir analogs) for carrying out the present invention include, but are not limited to:

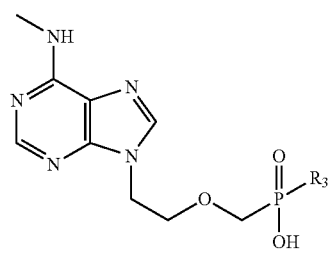

-continued
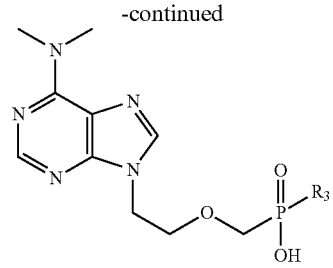
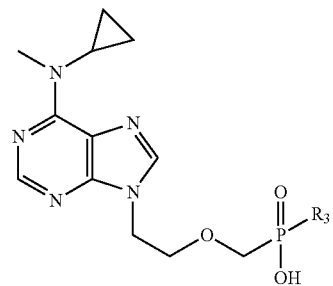
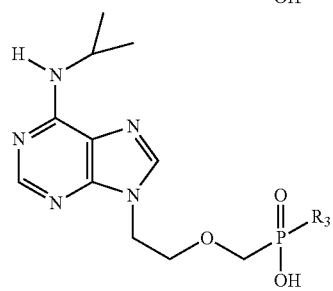
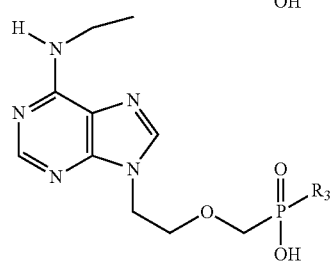
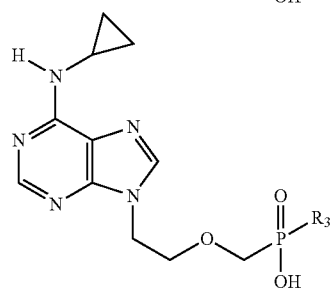
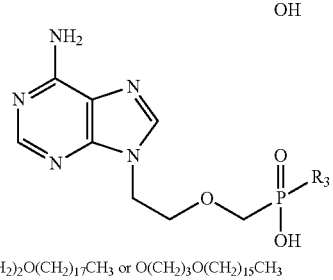
where R₃ is: $O(CH_2)_2O(CH_2)_{17}CH_3$ or $O(CH_2)_3O(CH_2)_{15}CH_3$
Additional examples of active compounds (HPMPA analogs) for carrying out the present invention include, but are not limited to:
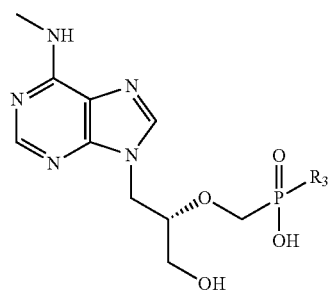
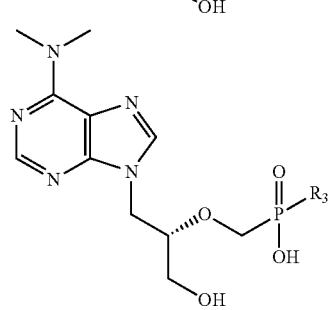
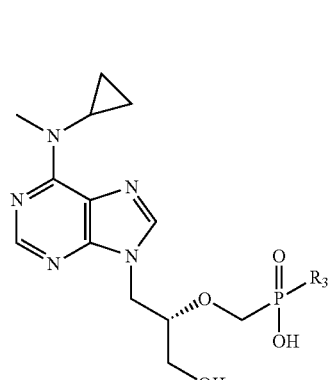
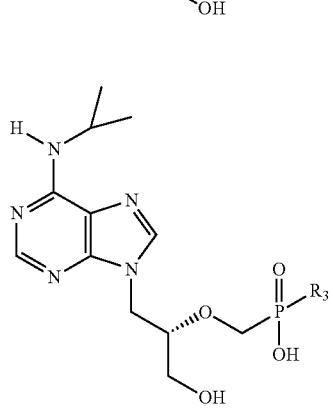
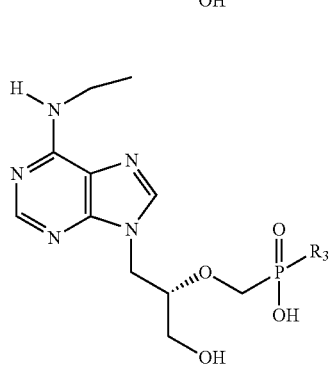

-continued

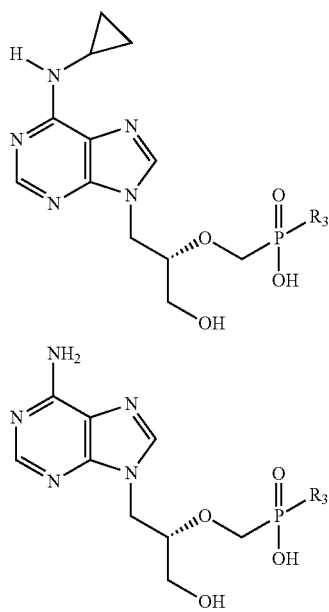

where $R_3$ is: $O(CH_2)_2O(CH_2)_{17}CH_3$ or $O(CH_2)_3O(CH_2)_{15}CH_3$

Additional examples of active compounds (PMEG analogs) useful for carrying out the present invention include, but are not limited to:

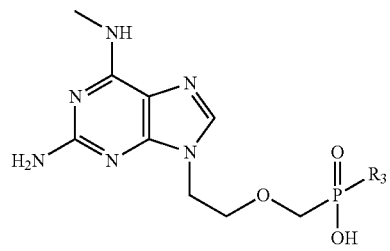

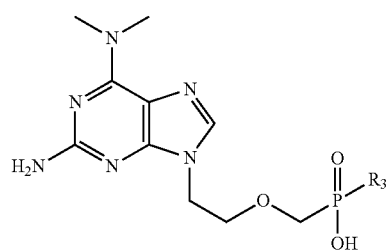

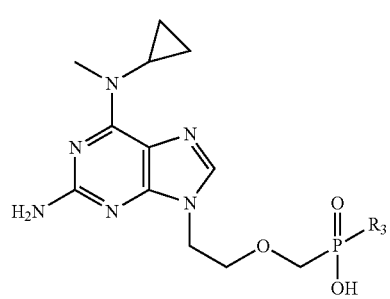

-continued

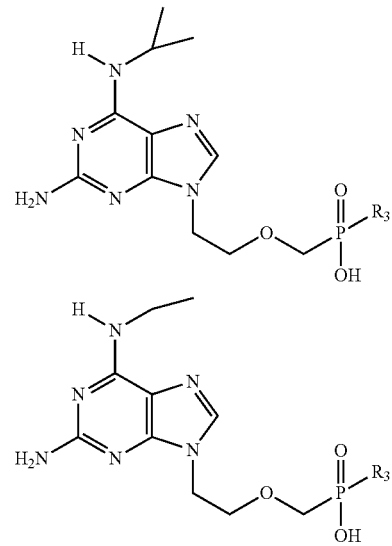

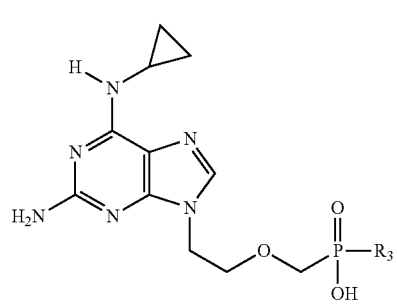

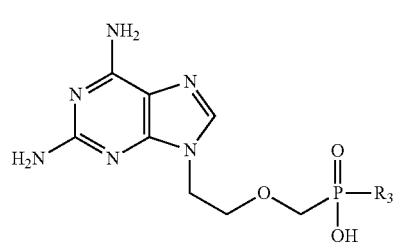

where $R_3$ is: $O(CH_2)_2O(CH_2)_{17}CH_3$ or $O(CH_2)_3O(CH_2)_{15}CH_3$

Thus, active compounds useful for carrying out the present invention include lipid tenofovir conjugates such as compounds of Formula II (or in some embodiments, more particularly as compounds of Formula IIa):

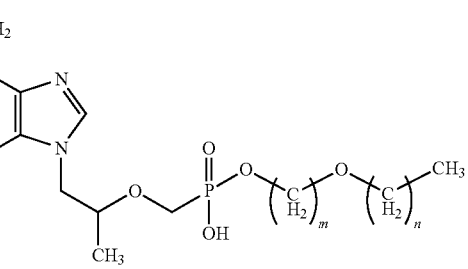

(II)

-continued

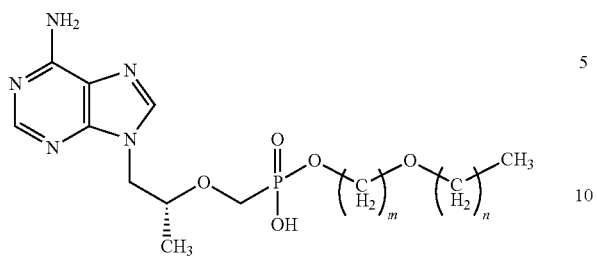
(IIa)

where m is from 2 to 5 (in some embodiments, 3) and n is from 11 to 21 (in some embodiments, 15 or 17), or a pharmaceutically acceptable salt, or a stereoisomer, a diastereomer, an enantiomer or racemate thereof.

An example of the compound is a compound of Formula III (also referred to as CMX157 herein):

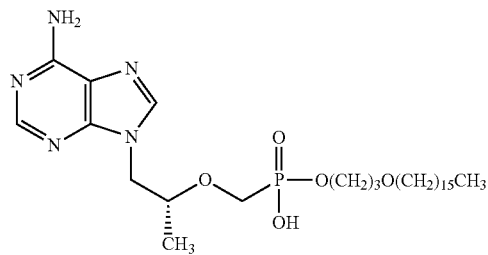
(III) CMX 157 or a pharmaceutically acceptable salt, or a stereoisomer, a diastereomer, an enantiomer or racemate thereof.

Such compounds are known and described in, for example, G. Painter et al., Evaluation of Hexadecyloxypropyl-9-R-[2-(Phosphonomethoxy)Propyl]-Adenine, CMX157, as a Potential Treatment for Human Immunodeficiency Virus Type 1 and Hepatitis B Virus Infections, *Antimicrobial Agents and Chemotherapy* 51, 3505-3509 (2007); U.S. Pat. No. 7,034,014 to Hostetler, and U.S. Pat. No. 6,716,825 to Hostetler, and/or can be prepared by modification of known techniques including but not limited to those described in PCT Patent Applications WO2005/79812 A1 (Anadys Pharmaceuticals) and WO2008/10921 A2 (Gilead).

In addition to the compounds described in connection with Formulas I-III above, a variety of lipid derivatives of acyclic nucleotide phosphonates such as tenofovir can be used as active agents in the methods and compositions provided herein. In one embodiment, the active agents have the following structures:

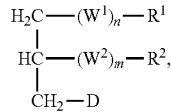
V

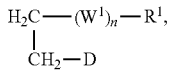
VI

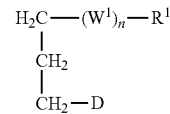
VII

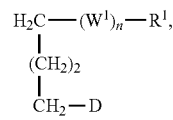
VIII

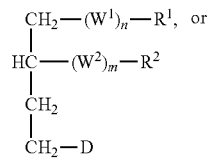
IX

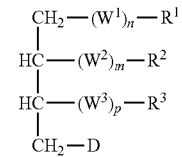
X wherein $W^1$, $W^2$, and $W^3$ are each independently —O—, —S—, —SO—, —SO$_2$—, —O(C=O)—, —(C=O)O—, —NH(C=O)—, —(C=O)NH— or —NH—; and in one embodiment are each independently O, S, or —O(C=O)—;

n is 0 or 1; m is 0 or 1; p is 0 or 1;

$R^1$ is an optionally substituted alkyl, alkenyl or alkynyl, e.g., $C_{1-30}$ alkyl, $C_{2-30}$ alkenyl, or $C_{2-30}$ alkynyl; or in one embodiment, $R^1$ is optionally substituted $C_{8-30}$ alkyl, $C_{8-30}$ alkenyl or $C_{8-30}$ alkynyl, or $R^1$ is a $C_{8-24}$ alkyl, $C_{8-24}$ alkenyl or $C_{8-24}$ alkynyl (e.g., $C_{17}$, $C_{18}$, $C_{19}$, $C_{20}$, $C_{21}$, $C_{22}$, $C_{23}$, or $C_{24}$ alkyl, alkenyl, or alkynyl);

$R^2$ and $R^3$ are each independently an optionally substituted $C_{1-25}$ alkyl, $C_{2-25}$ alkenyl, or $C_{2-25}$ alkynyl;

D may be tenofovir directly linked to a methylene group as depicted in Formulas V-X, e.g., D is a moiety of the formula:

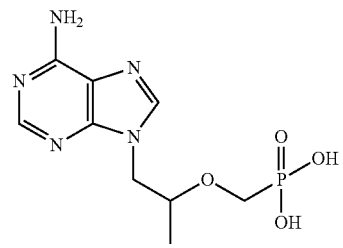 [SMILES: CC(Cn1cnc2c(N)ncnc21)OCP(=O)(O)O]

(e.g., Tenofovir is directly linked to the methylene group of formula V-X via the phosphonate hydroxyl group).

In some embodiments of Formulas V-X:

$W^1$, $W^2$, and $W^3$ are each independently —O—, —S—, or —O(CO)—;

n is 0 or 1; m is 0 or 1; p is 0 or 1;

$R^1$ is optionally substituted $C_{12-24}$ alkyl or alkenyl (e.g., $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, or $C_{24}$ alkyl or alkenyl);

$R^2$ and $R^3$ are each independently optionally substituted $C_{1-24}$ alkyl or $C_{2-24}$ alkenyl, or $C_{2-24}$ alkynyl.

D is tenofovir linked directly to a methylene group as depicted in Formulas V-X.

In another subembodiment, the active compound has one of the following structures: wherein $R^1$ is an optionally substituted $C_{8-24}$ alkyl, for example, $C_{12-24}$ alkyl, D is tenofovir linked directly to a methylene group as depicted in Formulas V-X.

The active compounds disclosed herein can, as noted above, be provided in the form of their pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of lithium, sodium and potassium, alkaline earth metal salts such as those of calcium and magnesium, and salts with organic bases such as dicyclohexylamine and N-methyl-D-glucamine.

Active compounds as described herein can be prepared in accordance with known procedures, or variations thereof that will be apparent to those skilled in the art. See, e.g., Painter et al., Evaluation of Hexadecyloxypropyl-9-R-[2-(Phosphonomethoxy)Propyl]-Adenine, CMX157, as a Potential Treatment for Human Immunodeficiency Virus Type 1 and Hepatitis B Virus Infections, *Antimicrobial Agents and Chemotherapy* 51, 3505-3509 (2007) and US Patent Application Publication No. 2007/0003516 to Almond et al.

B. Additional Antiviral Agents/Compounds.

Additional antiviral active agents that may be used in carrying out the present invention include HIV-protease inhibitors, nucleoside reverse transcriptase inhibitors (this term herein including nucleotide reverse transcriptase inhibitors), non-nucleoside reverse transcriptase inhibitors, integrase inhibitors, entry inhibitors, fusion inhibitors, maturation inhibitors, and combinations thereof. Numerous examples are known and described in, for Example, US Patent Application Publication No. 2006/0234982 to Dahl et al. at Table A therein, and in Table A as set forth below.

Additional examples include, but are not limited to the integrase inhibitor Isentress or raltegravir (MK-0518: Merck), the CCR5 inhibitor Maraviroc or selzentry (and K-427857, Pfizer) and others of these classes.

Additional examples are provided in U.S. Pat. No. 7,094, 413 to Buelow et al.; U.S. Pat. No. 7,250,421 to Nair et al., US Patent Application Publication No. 2007/0265227 to Heneine et al and US Patent Application Publication No. 2007/0072831 to Cai et al.

The non-nucleoside reverse transcriptase inhibitor ("NNRTI") 6-chloro-4-cyclopropylethynyl-4-trifluoromethyl-1,4-dihydro-2H3,1-benzoxazin-2-one, and pharmaceutically acceptable salts thereof, are described in, for example, U.S. Pat. No. 5,519,021. Examples of the present invention include efavirenz.

The nucleoside reverse transcriptase inhibitor ("NRTI") 2-hydroxymethyl-5-(5-fluorocytosin-1-yl)-1,3-oxathiolane ("FTC") and pharmaceutically acceptable salts thereof, are described in, for example, U.S. Pat. No. 6,642,245 to Liotta et al. Examples of the present invention include emtricitabine.

Integrase inhibitors include but are not limited to those described in US Patent Application Publication No. 2007/0072831, WO 02/30426, WO 02/30930, WO 02/30931, WO 02/055079, WO 02/36734, U.S. Pat. No. 6,395,743; U.S. Pat. No. 6,245,806; U.S. Pat. No. 6,271,402; WO 00/039086; WO 00/075122; WO 99/62513; WO 99/62520; WO 01/00578; Jing, et al., Biochemistry, 41, 5397-5403, (2002); Pais, et al., J. Med. Chem., 45, 3184-94 (2002); Goldgur, et al., Proc. Natl. Acad. Sci. U.S.A., 96, 13040-13043 (1999); Espeseth, et al., Proc. Natl. Acad. Sci. U.S.A., 97, 11244-11249, (2000); WO 2005/016927, WO 2004/096807, WO 2004/035577, WO 2004/035576 and US 2003/0055071.

TABLE A 5,6 dihydro-5-azacytidine
5-aza 2'deoxycytidine
5-azacytidine
5-yl-carbocyclic 2'-deoxyguanosine (BMS200,475)
9 (arabinofuranosyl)guanine; 9-(2'deoxyribofuranosyl)guanine
9-(2'-deoxy 2'fluororibofuranosyl)-2,6-diaminopurine
9-(2'-deoxy 2'fluororibofuranosyl)guanine
9-(2'-deoxyribofuranosyly-2,6 diaminopurine
9-(arabinofuranosyl)-2,6 diaminopurine
Abacavir, Ziagen ®
Acyclovir, ACV; 9-(2-hydroxyethoxylmethyl)guanine
Adefovir dipivoxil, Hepsera ®
amdoxivir, DAPD
Amprenavir, Agenerase ®
araA: 9-β-D-arabinofuranosyladenine (Vidarabine)
atazanivir sulfate (Reyataz ®)
AZT; 3'-azido-2',3'-dideoxythymdine, Zidovudine, (Retrovir ®)
BHCG; (.+−.)-(1a,2b,3a)-9-[2,3-bis(hydroxymethyl)cyclobutyl]guanine
BMS200,475; 5-yl-carbocyclic 2'-deoxyguanosine
Buciclovir; (R) 9-(3,4-dihydroxybutyl)guanine
BvaraU; 1-β-D-arabinofuranosyl-E-5-(2-bromovinyl)uracil (Sorivudinc)
Calanolide A
Capravirine
CDG: carbocyclic 2'-deoxyguanosine
Cidofovir, HPMPC; (S)-9-(3-hydroxy-2-phosphonylmethoxypropyl)cytosine
Clevudine, L-FMAU; 2'-Fluoro-5-methyl-β-L-arabino-furanosyluracil
Combivir ® (lamivudine/zidovudine)
Cytallene; [1-(4'-hydroxy-1',2'-butadienyl)cytosine]
d4C; 3'-deoxy-2',3'-didehydrocytidine
DAPD; (−)-β-D-2,6-diaminopurine dioxolane
ddA; 2',3'-dideoxyadenosine
ddAPR; 2,6-diaminopurine-2',3'-dideoxyriboside
ddC; 2',3'-dideoxycytidine (Zalacitabine)
ddI; 2',3'-dideoxyinosine, didanosine, (Videx ®, Videx ® EC)
Delavirdine, Rescriptor ®
Didanosine, ddI, Videx ®; 2',3'-dideoxyinosine
DXG; dioxolane guanosine
E-5-(2-bromovinyl)-2'-deoxyuridine
Efavirenz, Sustiva ®
Enfuvirtide, Fuzeon ®
F-ara-A; fluoroarabinosyladenosine (Fludarabine)
FDOC; (−)-β-D-5-fluoro-1-[2-(hydroxymethyl)-1,3-dioxolane]cytosine
FEAU: 2'-deoxy-2'-fluoro-1-β-D-arabinofuranosyl-5-ethyluracil
FIAC; 1-(2-deoxy-2-fluoro-β-D-arabinofuranosyl)-5-iodocytosine
FIAU; 1-(2-deoxy-2-fluoro-β-D-arabinofuranosyl)-5-iodouridine
FLG; 2',3'-dideoxy-3'-fluoroguanosine
FLT; 3'-deoxy-3'-fluorothymidine
Fludarabine; F-ara-A; fluoroarabinosyladenosine
FMAU: 2'-Fluoro-5-methyl-β-L-arabino-furanosyluracil
FMdC
Foscarnet; phosphonoformic acid, PFA
FPMPA; 9-(3-fluoro-2-phosphonylmethoxypropyl)adenine
Gancyclovir, GCV; 9-(1,3-dihydroxy-2-propoxymethyl)guanine
GS-7340; 9-[R-2-[[(S)-[[(S)-1-(isopropoxycarbonyl)ethyl]amino]-phenoxyphosphinypl methoxy]propyl]adenine
HPMPA; (S)-9-(3-hydroxy-2-phosphonylmethoxypropyl)adenine
HPMPC; (S)-9-(3-hydroxy-2-phosphonylmethoxypropyl)cytosine (Cidofovir)
Hydroxyurea, Droxia ®
Indinavir, Crixivan ®
Kaletra ® (lopinavir/ritonavir)
Lamivudine, 3TC, Epivir ™; (2R, 5S, cis)-4-amino-1-(2-hydroxymethyl-1,3-oxathiolan-5-yl)-(1H)-pyrimidin-2-one

TABLE A-continued

L-d4C; L-3'-deoxy-2',3'-didehydrocytidine
L-ddC; L-2',3'-dideoxycytidine
L-Fd4C; L-3'-deoxy-2',3'-didehydro-5-fluorocytidine
L-FddC; L-2',3'-dideoxy-5-fluorocytidine
Lopinavir
Nelfinavir, Viracept ®
Nevirapine, Viramune ®
Oxetanocin A; 9-(2-deoxy-2-hydroxymethyl-β-D-erythro-oxetanosyl)adenine
Oxetanocin G: 9-(2-deoxy-2-hydroxymethyl-β-D-erythro-oxetanosyl)guanine
Penciclovir
PMEDAP; 9-(2-phosphonylmethoxyethyl)-2,6-diaminopurine
PMPA, tenofovir; (R)-9-(2-phosphonylmethoxypropyl)adenine
PPA; phosphonoacetic acid
Ribavirin; 1-β-D-ribofuranosyl-1,2,4-triazole-3-carboxamide
Ritonavir, Norvir ®
Saquinavir, Invirase ®, Fortovase ®
Sorivudine, BvaraU; 1-β-D-arabinofuranosyl-E-5-(2-bromovinyl)uracil
Stavudine, d4T, Zerit ®; 2',3'-didehydro-3'-deoxythymidine
Trifluorothyimdine, TFT; Trifluorothymidine
Trizivir ® (abacavir sulfate/lamivudine/zidovudine)
Vidarabine, araA; 9-β-D-arabinofuranosyladenine
Viread ®, tenofovir disoproxil fumarate (DF), Bis POC PMPA, TDF; 2,4,6,8-Tetraoxa-5-phosphanonanedioic acid, 5-[[(1R)-2-(6-amino-9H-purin-9-yl)-1-methylethoxy]methyl]-, bis(1-methylethyl) ester, 5-oxide, (2E)-2-butenedioate (1:1)
Zalcitabine, Hivid ®, ddC; 2',3'-dideoxycytidine
Zidovudine, AZT, Retrovir ®; 3'-azido-2',3'-dideoxythymdine
Zonavir; 5-propynyl-1-arabinosyluracil C. Pharmaceutical Formulations and Administration.

Examples of pharmaceutically acceptable carriers and methods of manufacture for various compositions include but are not limited to those described in Remington's Pharmaceutical Sciences, 18th Ed., Mack Publishing Co. (1990) (See also US Patent Application US 2007/0072831).

The compounds of the invention may be formulated with conventional carriers, diluents and excipients, which will be selected in accord with ordinary practice. Tablets will contain excipients, glidants, fillers, binders, diluents and the like. Aqueous formulations are prepared in sterile form, and when intended for delivery by other than oral administration generally will be isotonic. Formulations optionally contain excipients such as those set forth in the "Handbook of Pharmaceutical Excipients" (1986) and include ascorbic acid and other antioxidants, chelating agents such as EDTA, carbohydrates such as dextrin, hydroxyalkylcellulose, hydroxyalkylmethylcellulose, stearic acid and the like.

Compounds of the invention and their physiologically acceptable salts (hereafter collectively referred to as the active ingredients) may be administered by any route appropriate to the condition to be treated, suitable routes including oral, rectal, nasal, topical (including ocular, buccal and sublingual), vaginal and parenteral (including subcutaneous, intramuscular, intravenous, intradermal, intrathecal and epidural). The preferred route of administration may vary with for example the condition of the recipient.

While it is possible for the active ingredients to be administered alone it is preferably to present them as pharmaceutical formulations. The formulations, both for veterinary and for human use, of the present invention comprise at least one active ingredient, as above defined, together with one or more pharmaceutically acceptable carriers (excipients, diluents, etc.) thereof and optionally other therapeutic ingredients. The carrier(s) must be "acceptable" in the sense of being compatible with the other ingredients of the formulation and not deleterious to the recipient thereof.

The formulations include those suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

For infections of the eye or other external tissues e.g. mouth and skin, the formulations are, in some embodiments, applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc), in some embodiments, 0.2 to 15% w/w and in other embodiments, 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG400) and mixtures thereof. The topical formulations may desirably include a compound which enhances absorption or penetration of the active ingredient through the skin or other affected areas. Examples of such dermal penetration enhancers include dimethylsulfoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. In some embodiments, a hydrophilic emulsifier is included together with a lipophilic emulsifier which acts as a stabilizer. In some embodiments, it includes both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the present invention include Tween™ 60, Span™ 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties, since the solubility of the active compound in most oils likely to be used in pharmaceutical emulsion formulations is very low. In some embodiments, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. In some embodiments, the active ingredient is present in such formulations in a concentration of 0.5 to 20%. In some embodiments, the active ingredient is present in a concentration of 0.5 to 10%. In some embodiments, the active ingredient is present in a concentration of about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for nasal administration wherein the carrier is a solid include a coarse powder having a particle size for example in the range 20 to 500 microns (including particle sizes in a range between 20 and 500 microns in increments of 5 microns such as 30 microns, 35 microns, etc), which is administered in the manner in which snuff is taken, i.e. by rapid inhalation through the nasal passage from a container of the powder held close up to the nose. Suitable formulations wherein the carrier is a liquid, for administration as for example a nasal spray or as nasal drops, include aqueous or oily solutions of the active ingredient. Formulations suitable for aerosol administration may be prepared according to conventional methods and may be delivered with other therapeutic agents such as pentamidine for treatment of pneumocystis pneumonia.

Formulations suitable for vaginal administration may be presented as pessaries, rings, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described. Preferred unit dosage formulations are those containing a daily dose or unit daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavoring agents.

The present invention further provides veterinary compositions comprising at least one active ingredient as above defined together with a veterinary carrier Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention can be used to provide controlled release pharmaceutical formulations containing as active ingredient one or more compounds of the invention ("controlled release formulations") in which the release of the active ingredient can be controlled and regulated to allow less frequent dosing or to improve the pharmacokinetic or toxicity profile of a given invention compound. Controlled release formulations adapted for oral administration in which discrete units comprising one or more compounds of the invention can be prepared according to conventional methods. Controlled release formulations may be employed for the treatment or prophylaxis of various microbial infections particularly human bacterial, human parasitic protozoan or human viral infections caused by microbial species including Plasmodium, Pneumocystis, herpes viruses (CMV, HSV 1, HSV 2, VZV, and the like), retroviruses, adenoviruses and the like. The controlled release formulations can be used to treat HIV infections and related conditions such as tuberculosis, malaria, pneumocystis pneumonia, CMV retinitis, AIDS, AIDS-related complex (ARC) and progressive generalized lymphadeopathy (PGL), and AIDS-related neurological conditions such as multiple sclerosis, and tropical spastic paraparesis. Other human retroviral infections that may be treated with the controlled release formulations according to the invention include Human T-cell Lymphotropic virus and HIV-2 infections. The invention accordingly provides pharmaceutical formulations for use in the treatment or prophylaxis of the above-mentioned human or veterinary conditions and microbial infections.

Pharmacokinetic Enhancers.

The compounds of the invention may be employed in combination with pharmacokinetic enhancers (sometimes also referred to as "booster agents"). One aspect of the invention provides the use of an effective amount of an enhancer to enhance or "boost" the pharmacokinetics of a compound of the invention. An effective amount of an enhancer, for example, the amount required to enhance an active compound or additional active compound of the invention, is the amount necessary to improve the pharmacokinetic profile or activity of the compound when compared to its profile when used alone. The compound possesses a better efficacious pharmacokinetic profile than it would without the addition of the enhancer. The amount of pharmacokinetic enhancer used to enhance the potency of the compound is, preferably, sub-therapeutic (e.g., dosages below the amount of booster agent conventionally used for therapeutically treating infection in a patient). An enhancing dose for the compounds of the invention is subtherapeutic for treating infection, yet high enough to effect modulation of the metabolism of the compounds of the invention, such that their exposure in a patient is boosted by increased bioavailability, increased blood levels, increased half life, increased time to peak plasma concentration, increased/faster inhibition of HIV integrase, RT or protease and/or reduced systematic clearance. One example of a pharmacokinetic enhancer is RITONAVIR™ (Abbott Laboratories).

Combinations.

As noted above, the compositions of the present invention can include the active compounds as described in section A above in combination with one or more (e.g., 1, 2, 3) additional active agents such as described in section B above, in analogous manner as known in the art. For example, combinations of efavirenz (an NRTI), emtricitabine (an NNRTI) and tenofovir DF (an NRTI) are described in, for example, Dahl et al., US Patent Application Publication No. 2007/0099902 to Dahl et al. Specific examples of such combinations include, but are not limited to: CMX 157 or a pharmaceutically acceptable salt) in combination with:

(a) FTC/Efavirenz;
(b) 3TC/Efavirenz;
(c) AZT/3TC;
(d) FTC;
(e) 3TC;
(f) FTC/Isentress;
(g) 3TC/Isentress;
(h) PPL-100;
(i) FTC/TMC278;
(k) 3TC/TMC278;
(l) FTC/TMC125; or
(m) 3TC/TMC125.

D. Treatment of Privileged Compartment Infections.

As noted above, it has also been found that active agents of the present invention surprisingly associate or bind to viral particles. Since viral particles migrate or permeate into cellular or tissue compartments that are not generally accessible to active therapeutic agents (thus creating a substantially untreated "reservoir" of infection when subjects are systemically administered such agents), this finding makes possible (a) the treatment of infection in such privileged compartments, and (b) the use of active agents in prophylactic or microbicidal treatments (where association or binding of the active agent to virus before infection occurs is of therapeutic benefit).

In general, a privileged compartment is a cellular or tissue compartment to which said virus permeates in vivo, to which said active agent does not efficiently permeate in vivo in the absence of said virus, and to which said active agent is carried in vivo by said virus when said active agent binds to said virus. For example, when the privileged compartment is a tissue compartment, it may be brain (central nervous system), lymphoid, or testes. Examples of cellular privileged compartments include but are not limited to dendritic cells, microglia, monocyte/macrophages, and combinations thereof. Compositions and methods of treating privileged compartment infections may be prepared and carried out as described above. Prophylactic compositions, devices and methods are discussed in further detail below.

E. Topical Compositions and Microbicidal Methods.

The present invention can take the form of a topical compositions containing the active agents described herein for inhibiting or combating viral infection, e.g., for prophylactic use. Such compositions (with active agents other than those disclosed herein) are known and described in, for example, U.S. Pat. No. 6,545,007, the disclosure of which is incorporated herein by reference in its entirety.

Such compositions can take several forms. Thus, in one embodiment the composition is in the form of a cream, lotion, gel, or foam that is applied to the affected skin or epithelial cavity, and preferably spread over the entire skin or epithelial surface which is at risk of contact with bodily fluids. Such formulations, which are suitable for vaginal or rectal administration, may be present as aqueous or oily suspensions, solutions or emulsions (liquid formulations) containing in addition to the active ingredient, such carriers as are known in the art to be appropriate. For "stand-alone" lubricants (i.e., lubricants that are not pre-packaged with condoms), gels and similar aqueous formulations are generally preferred, for various reasons (both scientific and economic) known to those skilled in the art. These formulations are useful to protect not only against sexual transmission of HIV, but also to prevent infection of a baby during passage through the birth canal. Thus the vaginal administration can take place prior to sexual intercourse, during sexual intercourse, and immediately prior to childbirth.

One method of applying an antiviral lubricant to the genitals, for the purposes disclosed herein, involves removing a small quantity (such as a teaspoon, or several milliliters) of a gel, cream, ointment, emulsion, or similar formulation from a plastic or metallic tube, jar, or similar container, or from a sealed plastic, metallic or other packet containing a single dose of such composition, and spreading the composition across the surface of the penis immediately before intercourse. Alternate methods of emplacement include: (1) spreading the composition upon accessible surfaces inside the vagina or rectum shortly before intercourse; and (2) emplacing a condom, diaphragm, or similar device, which has already been coated or otherwise contacted with an antiviral lubricant, upon the penis or inside the vagina. In a preferred embodiment, any of these methods of spreading an anti-viral lubricant across the surfaces of the genitals causes the lubricant to coat and remain in contact with the genital and epithelial surfaces throughout intercourse.

In one embodiment the compositions are used in conjunction with condoms, to enhance the risk-reducing effectiveness of condoms and provide maximum protection for users. The composition can either be coated onto condoms during manufacture, and enclosed within conventional watertight plastic or foil packages that contain one condom per package, or it can be manually applied by a user to either the inside or the outside of a condom, immediately before use.

As used herein, "condom" refers to a barrier device which is used to provide a watertight physical barrier between male and female genitalia during sexual intercourse, and which is removed after intercourse. This term includes conventional condoms that cover the penis; it also includes so-called "female condoms" which are inserted into the vaginal cavity prior to intercourse. The term "condom" does not include diaphragms, cervical caps or other barrier devices that cover only a portion of the epithelial membranes inside the vaginal cavity. Preferably, condoms should be made of latex or a synthetic plastic material such as polyurethane, since these provide a high degree of protection against viruses.

In another embodiment the composition is in the form of an intra-vaginal pill, an intra-rectal pill, or a suppository. The suppository or pill should be inserted into the vaginal or rectal cavity in a manner that permits the suppository or pill, as it dissolves or erodes, to coat the vaginal or rectal walls with a prophylactic layer of the anti-HIV agent.

In still another embodiment the composition is topically applied by release from an intravaginal device. Devices such as vaginal rings, vaginal sponges, diaphragms, cervical caps, female condoms, and the like can be readily adapted to release the composition into the vaginal cavity after insertion.

Compositions used in the methods of this invention may also comprise additional active agents, such as another agent (s) to prevent HIV infection, and agents that protect individuals from conception and other sexually transmitted diseases. Thus, in another embodiment, the compositions used in this invention further comprise one or more additional anti-HIV agents, virucides effective against viral infections other than HIV, and/or spermicides.

In one particular embodiment, the composition contains nonoxynol, a widely-used spermicidal surfactant. The resulting composition could be regarded as a "bi-functional" composition, since it would have two active agents that provide two different desired functions, in a relatively inert carrier liquid; the nonoxynol would provide a spermicidal contraceptive agent, and the DABO would provide anti-viral properties. The nonoxynol is likely to cause some level of irritation, in at least some users; this is a regrettable but is a well-known side effect of spermicidal surfactants such as nonoxynol and octoxynol, which attack and destroy the lipid bilayer membranes that surround sperm cells and other mammalian cells.

The compositions used in this invention may also contain a lubricant that facilitates application of the composition to the desired areas of skin and epithelial tissue, and reduces friction during sexual intercourse. In the case of a pill or suppository, the lubricant can be applied to the exterior of the dosage form to facilitate insertion.

In still another embodiment the invention provides a device for inhibiting the sexual transmission of HIV comprising (a) a barrier structure for insertion into the vaginal cavity, and (b) a composition comprising an active agent as described herein.

As mentioned above, preferred devices which act as barrier structures, and which can be adapted to apply anti-HIV agent, include the vaginal sponge, diaphragm, cervical cap, or condom (male or female).

The methods, compositions and devices of this invention can be adapted generally to release active agent in a time sensitive manner that best corresponds to the timing of sexual activity. When topically applied as a lotion or gel, the compositions are preferably applied immediately prior to sexual activity. Other modes of application, such as devices and suppositories, can be designed to release active agent over a prolonged period of time, at a predetermined rate, depending upon the needs of the consumer.

The present invention will now be described in more detail with reference to the following examples. However, these examples are given for the purpose of illustration and are not to be construed as limiting the scope of the invention

EXAMPLE 1

FIG. 1 demonstrates, for comparative purposes, the virologic response to tenofovir in antiretroviral experienced patients at 24 weeks. Data is from M. Miller et al. *J Infect Dis.* 189: 837 (2004). The viral load response in monotherapy with TDF in naïve patients is −1.5 log (Louie et al, *Determining the antiviral activity of tenofovir disoproxil fumarate in treatment-naive chronically HIV-1-infected individuals*, AIDS, 17, 1151 (2003)).

Figure 2:
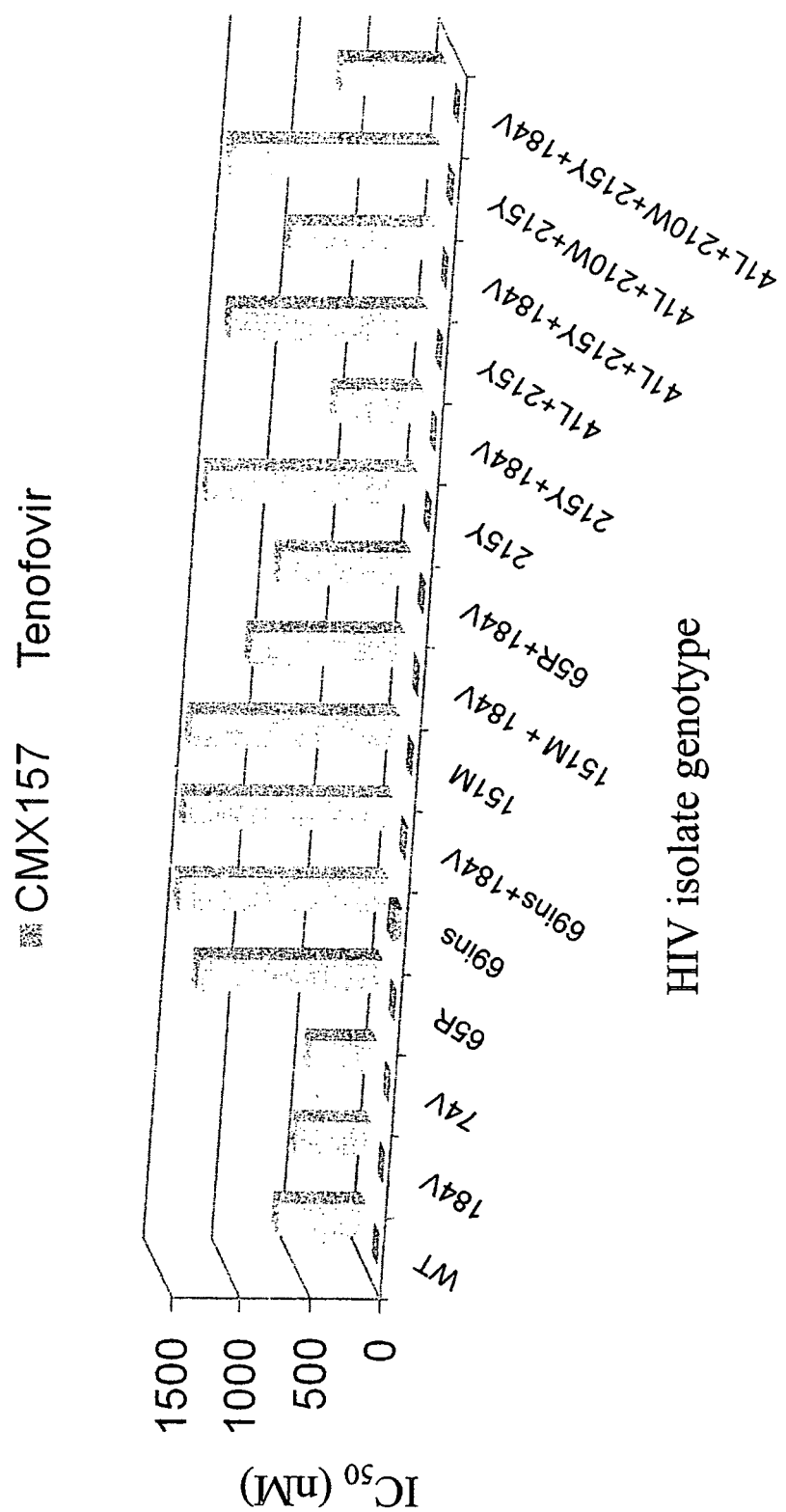
FIG. 2 shows the in vitro efficacy of tenofovir (TFV) as compared to HDP-TFV (CMX157).
Figure 3:
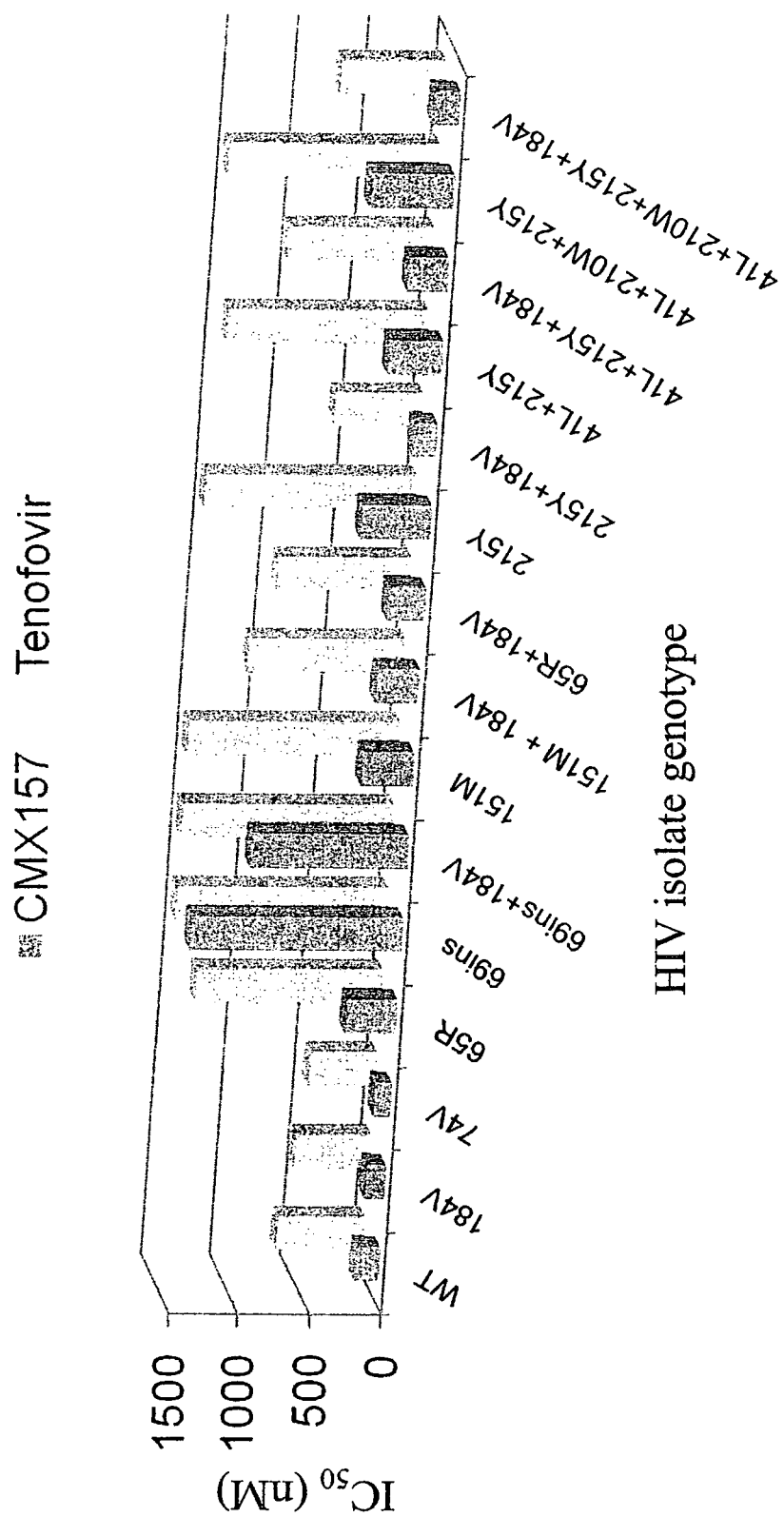
FIG. 3 shows the in vitro efficacy of TFV as compared to HDP-TFV (CMX157), this time with the $IC_{50}$s for HDP-TFV multiplied by 100 for scaling.

FIGS. 2-3 show the in vitro efficacy of tenofovir (TFV) as compared to HDP-TFV (CMX157) in a PHENOSENSE™ HIV assay (service available from Monogram Biosciences, Inc., 345 Oyster Point Blvd., South San Francisco, Calif. 94080-1913 USA.) In FIG. 3, the $IC_{50}$s for CMX157 are multiplied by 100 for scaling. Results are also shown in Table 1 below (where ABC is abacavir FTC is emtricitabine, ddI is didanosine, 3TC is lamivudine, d4T is stavudine, TFV is tenofovir and ZDV is zidovudine).

TABLE 1

ASSAY RESULTS (IC50 shown in μM)

| PATIENT ID | NOTES | Results | ABC | CMX157 | ddI | FTC | 3TC | d4T | TFV | ZDV |
|---|---|---|---|---|---|---|---|---|---|---|
| PANEL 1 | WT | IC50 Fold Change | 0.86 | 0.93 | 1.01 | 0.78 | 0.86 | 0.86 | 0.79 | 0.72 |
|  |  | IC50 | 1.520000 | 0.001720 | 5.540000 | 0.890000 | 3.240000 | 0.510000 | 0.613000 | 0.020000 |
| PANEL 2 | WT | IC50 Fold Change | 0.94 | 0.87 | 1.01 | 1.38 | 1.18 | 0.81 | 0.85 | 0.61 |
|  |  | IC50 | 1.670000 | 0.001610 | 5.570000 | 1.570000 | 4.440000 | 0.480000 | 0.652000 | 0.017000 |
| PANEL 3 | 6 TAMs, no 184 | IC50 Fold Change | 4.43 | 4.58 | 1.59 | 5.02 | 3.70 | 3.66 | 3.47 | 350.00 |
|  |  | IC50 | 7.870000 | 0.008500 | 8.760000 | 5.730000 | 13.930000 | 2.170000 | 2.674000 | 9.562000 |
| PANEL 6 | 6 TAMs + 184 | IC50 Fold Change | 7.91 | 2.81 | 2.06 | >87.6048 | >79.7162 | 2.28 | 2.16 | 59.00 |
|  |  | IC50 | 14.040000 | 0.005210 | 11.350000 | >100 | >300 | 1.350000 | 1.666000 | 1.610000 |
| PANEL 7 | 184V | IC50 Fold Change | 2.69 | 0.73 | 1.38 | >87.6048 | >79.7162 | 0.77 | 0.69 | 0.63 |
|  |  | IC50 | 4.780000 | 0.001360 | 7.570000 | >100 | >300 | 0.460000 | 0.534000 | 0.017000 |
| PANEL 9 | 69ins, no 184 | IC50 Fold Change | 18.00 | 31.00 | 4.04 | 26.00 | 12.00 | 11.00 | 22.00 | >915.7073 |
|  |  | IC50 | 32.650000 | 0.057430 | 22.210000 | 29.600000 | 45.880000 | 6.390000 | 16.959000 | >25 |
| PANEL 12 | 69ins + 184 | IC50 Fold Change | 26.00 | 6.06 | 4.43 | >87.6048 | >79.7162 | 11.00 | 4.72 | 319.00 |
|  |  | IC50 | 46.540000 | 0.011230 | 24.330000 | >100 | >300 | 6.790000 | 3.641000 | 8.711000 |
| PANEL 14 | 65R, no 184 | IC50 Fold Change | 3.20 | 1.94 | 1.67 | 17.00 | 19.00 | 1.30 | 1.71 | 0.44 |
|  |  | IC50 | 5.690000 | 0.003600 | 9.170000 | 19.330000 | 70.840000 | 0.770000 | 1.319000 | 0.012000 |
| PANEL 15 | 65R + 184V | IC50 Fold Change | 6.64 | 1.46 | 2.61 | >87.6048 | >79.7162 | 0.99 | 1.22 | 0.41 |
|  |  | IC50 | 11.780000 | 0.002710 | 14.330000 | >100 | >300 | 0.590000 | 0.940000 | 0.011000 |

TABLE 1-continued

ASSAY RESULTS (IC50 shown in μM)

| PATIENT ID | NOTES | Results | ABC | CMX157 | ddI | FTC | 3TC | d4T | TFV | ZDV |
|---|---|---|---|---|---|---|---|---|---|---|
| PANEL 17 | L74V | IC50 Fold Change | 1.89 | 0.66 | 1.63 | 1.87 | 1.85 | 1.01 | 0.62 | 0.41 |
| | | IC50 | 3.360000 | 0.001230 | 8.940000 | 2.140000 | 6.980000 | 0.600000 | 0.476000 | 0.011000 |
| PANEL 19 | L74V + M184V | IC50 Fold Change | 5.21 | 0.36 | 2.01 | >87.6048 | >79.7162 | 0.71 | 0.29 | 0.22 |
| | | IC50 | 9.240000 | 0.000660 | 11.060000 | >100 | >300 | 0.420000 | 0.227000 | 0.006000 |
| PANEL 26 | 151M, no 184 | IC50 Fold Change | 19.00 | 1.99 | 12.00 | 30.00 | 24.00 | 9.33 | 2.26 | 93.00 |
| | | IC50 | 34.310000 | 0.003680 | 63.250000 | 34.730000 | 89.620000 | 5.540000 | 1.739000 | 2.545000 |
| PANEL 28 | 151M + 184 | IC50 Fold Change | >29.2959 | 1.64 | 11.00 | >87.6048 | >79.7162 | 7.10 | 1.43 | 153.00 |
| | | IC50 | >52 | 0.003050 | 58.040000 | >100 | >300 | 4.220000 | 1.102000 | 4.179000 |
| PANEL 29 | L74V – SDM | IC50 Fold Change | 1.85 | 0.80 | 1.48 | 1.47 | 1.62 | 1.07 | 0.69 | 0.50 |
| | | IC50 | 3.290000 | 0.001480 | 8.140000 | 1.680000 | 6.100000 | 0.630000 | 0.535000 | 0.014000 |
| PANEL 30 | M184V – SDM | IC50 Fold Change | 2.64 | 0.62 | 1.23 | >87.6048 | >79.7162 | 0.68 | 0.54 | 0.34 |
| | | IC50 | 4.680000 | 0.001150 | 6.760000 | >100 | >300 | 0.400000 | 0.413000 | 0.009000 |
| PANEL 31 | K65R – SDM | IC50 Fold Change | 2.57 | 2.55 | 2.00 | 11.00 | 12.00 | 1.40 | 2.01 | 0.51 |
| | | IC50 | 4.560000 | 0.004730 | 11.020000 | 12.900000 | 43.330000 | 0.830000 | 1.551000 | 0.014000 |
| PANEL 33 | T215Y | IC50 Fold Change | 2.06 | 2.70 | 1.14 | 2.31 | 1.63 | 1.40 | 2.39 | 38.00 |
| | | IC50 | 3.670000 | 0.005000 | 6.290000 | 2.640000 | 6.120000 | 0.830000 | 1.843000 | 1.049000 |
| PANEL 34 | T215Y + M184V | IC50 Fold Change | 4.29 | 0.90 | 1.43 | >87.6048 | >79.7162 | 1.10 | 0.81 | 2.61 |
| | | IC50 | 7.610000 | 0.001670 | 7.880000 | >100 | >300 | 0.650000 | 0.624000 | 0.071000 |
| PANEL 35 | M41L + T215Y | IC50 Fold Change | 1.89 | 2.11 | 1.14 | 2.74 | 2.01 | 1.41 | 1.84 | 20.00 |
| | | IC50 | 3.360000 | 0.003910 | 6.290000 | 3.130000 | 7.550000 | 0.840000 | 1.421000 | 0.557000 |
| PANEL 37 | M41L + T215Y + M184V | IC50 Fold Change | 5.41 | 1.55 | 1.84 | >87.6048 | >79.7162 | 1.46 | 1.34 | 6.48 |
| | | IC50 | 9.600000 | 0.002880 | 10.120000 | >100 | >300 | 0.860000 | 1.034000 | 0.177000 |
| PANEL 38 | M41L + L210W + T215Y | IC50 Fold Change | 2.80 | 3.21 | 1.36 | 3.70 | 2.74 | 2.06 | 2.80 | 100.00 |
| | | IC50 | 4.970000 | 0.005960 | 7.500000 | 4.220000 | 10.320000 | 1.220000 | 2.155000 | 2.722000 |
| PANEL 39 | M41L + L210W + T215Y | IC50 Fold Change | 2.36 | 3.54 | 1.07 | 1.89 | 1.57 | 1.84 | 3.01 | 98.00 |
| | | IC50 | 4.190000 | 0.006560 | 5.900000 | 2.160000 | 5.890000 | 1.090000 | 2.322000 | 2.677000 |
| PANEL 40 | M41L + L210W + T215Y + M184V | IC50 Fold Change | 4.60 | 1.02 | 1.49 | >87.6048 | >79.7162 | 1.48 | 0.97 | 3.18 |
| | | IC50 | 8.170000 | 0.001890 | 8.180000 | >100 | >300 | 0.880000 | 0.751000 | 0.087000 |
| PANEL 41 | M41L + L210W + T215Y + M184V | IC50 Fold Change | 5.02 | 1.35 | 1.57 | >87.6048 | >79.7162 | 1.77 | 1.02 | 3.91 |
| | | IC50 | 8.920000 | 0.002500 | 8.640000 | >100 | >300 | 1.050000 | 0.789000 | 0.107000 |
| PANEL 42 | D67N + K70R | IC50 Fold Change | 1.40 | 3.03 | 1.19 | 2.87 | 2.14 | 1.31 | 2.56 | 28.00 |
| | | IC50 | 2.480000 | 0.005610 | 6.570000 | 3.280000 | 8.070000 | 0.780000 | 1.971000 | 0.770000 |
| PANEL 44 | D67N + K70R + T215F + K219E + M184V | IC50 Fold Change | 4.36 | 1.03 | 1.57 | >87.6048 | >79.7162 | 1.32 | 0.91 | 7.04 |
| | | IC50 | 7.730000 | 0.001920 | 8.650000 | >100 | >300 | 0.790000 | 0.703000 | 0.192000 |
| PANEL 45 | L210W + T215Y | IC50 Fold Change | 2.05 | 1.50 | 1.00 | 2.29 | 1.93 | 1.58 | 1.34 | 7.58 |
| | | IC50 | 3.640000 | 0.002790 | 5.510000 | 2.620000 | 7.260000 | 0.940000 | 1.033000 | 0.207000 |
| PANEL 46 | D67N + K70E | IC50 Fold Change | 1.36 | 1.15 | 1.41 | 2.97 | 2.87 | 0.94 | 0.96 | 0.21 |
| | | IC50 | 2.420000 | 0.002120 | 7.730000 | 3.390000 | 10.800000 | 0.560000 | 0.738000 | 0.006000 |
| PANEL 47 | D67N + K70E + M184V | IC50 Fold Change | 2.85 | 0.78 | 1.32 | >87.6048 | >79.7162 | 0.70 | 0.64 | 0.15 |
| | | IC50 | 5.050000 | 0.001450 | 7.250000 | >100 | >300 | 0.420000 | 0.495000 | 0.004000 |
| PANEL 48 | K70E + M184V | IC50 Fold Change | 5.88 | 0.71 | 1.80 | >87.6048 | >79.7162 | 0.65 | 0.61 | 0.13 |
| | | IC50 | 10.440000 | 0.001320 | 9.910000 | >100 | >300 | 0.390000 | 0.472000 | 0.004000 |

The data shown in Tables 2 and 3 below demonstrate that CMX157 is active against all major HIV subtypes (A-G, O and HIV-2) with $IC_{50}$s ranging from 0.2-7.2 nanomolar.

TABLE 2

Activity of Chimerix Compound CMX157 Against HIV-1 Subtype Isolates in PBMCs

| HIV-1 Isolate | Subtype | RT Endpoint | | |
|---|---|---|---|---|
| | | $IC_{50}$ (nM) | $TC_{50}$ (nM) | TI ($TC_{50}/IC_{50}$) |
| RW/92/009 | A | 1.75 | >1,000 | >571 |
| UG/92/029 | A | 5.84 | >1,000 | >171 |
| UG/92/037 | A | 2.30 | >1,000 | >435 |
| ADA | B | 1.08 | >1,000 | >925 |
| BR/92/014 | B | 1.58 | >1,000 | >633 |
| 96USHIPS7 | B | 4.80 | >1,000 | >208 |
| JR-CSF | B | 0.68 | >1,000 | >1,480 |
| TH/92/026 | B | 0.44 | >1,000 | >2,278 |
| BR/92/025 | C | 3.43 | >1,000 | >291 |

TABLE 2-continued

Activity of Chimerix Compound CMX157 Against HIV-1 Subtype Isolates in PBMCs

| HIV-1 Isolate | Subtype | RT Endpoint | | |
|---|---|---|---|---|
| | | $IC_{50}$ (nM) | $TC_{50}$ (nM) | TI ($TC_{50}/IC_{50}$) |
| IN/93/101 | C | 0.53 | >1,000 | >1,892 |
| MW/93/959 | C | 4.50 | >1,000 | >222 |
| UG/92/001 | D | 5.16 | >1,000 | >194 |
| UG/92/024 | D | 0.30 | >1,000 | >3,346 |
| UG/92/046 | D | 0.96 | >1,000 | >1,039 |
| TH/93/073 | E | 2.95 | >1,000 | >339 |
| CMU08 | E | 2.81 | >1,000 | >356 |
| CMU06 | E | 1.03 | >1,000 | >970 |
| BR/93/019 | F | 6.40 | >1,000 | >156 |
| BR/93/020 | F | 0.73 | >1,000 | >1,362 |
| BR/93/029 | F | 1.03 | >1,000 | >972 |
| JV1083 | G | 2.32 | >1,000 | >431 |
| RU132 | G | 1.63 | >1,000 | >615 |
| G3 | G | 2.68 | >1,000 | >373 |
| BCF01 | O | 7.18 | >1,000 | >139 |
| BCF02 | O | 2.47 | >1,000 | >405 |
| BCF03 | O | 5.29 | >1,000 | >189 |

TABLE 3

Activity of Chimerix Compound CMX157 against HIV-2 Isolates in PBMCs

| HIV-2 Isolate | RT Endpoint | | |
|---|---|---|---|
| | $IC_{50}$ (nM) | $TC_{50}$ (nM) | TI ($TC_{50}/IC_{50}$) |
| CDC310319 | 1.77 | >1,000 | >564 |
| CDC310342 | 4.31 | >1,000 | >232 |
| CBL-20 | 4.48 | >1,000 | >223 |

Further, these data indicate that the $IC_{50}$s for CMX157 against NRTI resistant HIV ranged from 1.2 to 57 nM, a median of 359-fold more potent than tenofovir (range 295-472x).

Finally, the data shown in Table 4 below indicates that the no-observed-adverse-effect level in rats for CMX157 for 7 days is up to 100 mg/kg/day, the highest dose tested.

TABLE 4

Toxicokinetic parameters on days 1 and 7 after oral administration of CMX157 to rats

| | | CMX157 (prodrug) | | | | | Tenofovir (metabolite) | | | | |
|---|---|---|---|---|---|---|---|---|---|---|---|
| Day | Dose (mg/kg) | Cmax (ng/ml) | Tmax (h) | $AUC_{0-24}$ (ng·h/ml) | $AUC_{0-\infty}$ (ng·h/ml) | $t_{1/2elim}$ (h) | Cmax (ng/ml) | Tmax (h) | $AUC_{0-24}$ (ng·h/ml) | $AUC_{0-\infty}$ (ng·h/ml) | $t_{1/2elim}$ (h) |
| 1 | 10 | 84.85 | 0.5 | 441.7 | ND | ND | 55.35 | 2.0 | 510.8 | 775.2 | 10.9 |
| 7 | 10 | 110.90 | 0.5 | 435.2 | ND | ND | 49.55 | 2.4 | 964.7 | 1,226.9 | 9.2 |
| 1 | 30 | 379.00 | 2.0 | 1,832.8 | ND | ND | 109.10 | 4.0 | 1,456.1 | 1,808.1 | 10.1 |
| 7 | 30 | 202.50 | 1.0 | 1,543.9 | ND | ND | 149.25 | 4.0 | 2,363.4 | 2,790.5 | 7.6 |
| 1 | 100 | 905.00 | 2.0 | 5,408 | 5,429.8 | 2.5 | 181.40 | 12.0 | 3,039.3 | 3,639.5 | 7.2 |
| 7 | 100 | 685.50 | 2.0 | 8,046.3 | 8,050.6 | 1.6 | 322.00 | 12.0 | 5,715.4 | 7,373.4 | 9.0 |

<sup>a</sup>Plasma was obtained at 0.5, 1, 2, 4, 12, and 24 h after dosing and assayed for the prodrug and metabolite as described in Materials and Methods. Pharmacokinetic parameters were estimated using mean data from one male and one female in each group at each time point. $AUC_{0-24}$, AUC from 0 to 24 h; $t_{1/2elim}$, elimination half-life; ND, not determined (See G. Painter et al., Evaluation of Hexadecyloxypropyl-9-R-[2-(Phosphonomethoxy)Propyl]-Adenine, CMX157, as a Potential Treatment for Human Immunodeficiency Virus Type 1 and Hepatitis B Virus Infections, *Antimicrobial Agents and Chemotherapy* 51, 3505-3509 (2007).)

EXAMPLE 2

To examine the potential of CMX157 to associate directly with virus, concentrated HIV-1$_{IIIB}$ (approximately 9.7×10$^{10}$ virus particles) is treated with 500 nM CMX157 or TFV for 2 hours. Following incubation, virus is pelleted to remove unbound compound, lysed with 70% ice cold methanol and centrifuged. Supernatants are analyzed in triplicate using LC/MS/MS (liquid chromatography/mass spectrometry). TFV, TFV mono- and diphosphate are separated by gradient, reverse phase, ion-paring chromatography and detected by positive ion electrospray. The levels of CMX157 associated with the viral pellets (≈37,000 molecules/virion) are much higher than the levels of TFV associated with viral pellets (≈100 molecules/virion).

To evaluate the effect of exposing purified virus to drug on $TCID_{50}$, concentrated HIV-1$_{IIIB}$ virus (approximately 9.7×10$^{10}$ virus particles) is treated with 1000, 500, 250 or 125 nM CMX157 or TFV for 2 hours. As shown in Table 5, CMX157 consistently reduce viral replication 2-4 fold across this dose range while TFV has no discernible effect even at the highest dose.

TABLE 5

TCID$_{50}$ Determination of Treated HIV-1$_{IIIB}$ (2 hours)

| Drug (nM) | CMX157 (Fold Decrease From VC*) | | | TFV (Fold Decrease From VC) | | |
|---|---|---|---|---|---|---|
| | XTT Endpoint | RT Endpoint | P24 Endpoint | XTT Endpoint | RT Endpoint | P24 Endpoint |
| 1000 | 1132 (4.0) | 36227 (2.2) | 7604 (4.8) | 4529 (0) | 64570 (1.3) | 36227 (0) |
| 500 | 1132 (4.0) | 36227 (2.2) | 7604 (4.8) | 4529 (0) | 81289 (0) | 37328 (0) |
| 250 | 1132 (4.0) | 25588 (3.2) | 10765 (3.4) | 4529 (0) | 72449 (1.1) | 36227 (0) |
| 125 | 1132 (4.0) | 51172 (1.6) | 9058 (4.0) | 4027 (1.1) | 72449 (1.1) | 43056 (0) |
| 0 | 4529 | 81289 | 36227 | 4529 | 81289 | 36227 |

*VC = vehicle control

To determine the time dependence of compound incubation on loss of infectivity, concentrated HIV-1$_{IIIB}$ is treated with 500 nM CMX157 for 1, 15, 30, 60, and 120 minutes. The TCID$_{50}$ results of these assays are summarized in Table 6. CMX157 decreases infectivity following 1 minute incubation prior to centrifugation.

TABLE 6

TCID$_{50}$ Determination of Treated HIV-1$_{IIIB}$

| Time of Compound Removal | Untreated Virus | | | CMX157 500 nM (Fold Decrease From VC*) | | |
|---|---|---|---|---|---|---|
| | XTT Endpoint | RT Endpoint | P24 Endpoint | XTT Endpoint | RT Endpoint | P24 Endpoint |
| 1 minute | 4529 | 132749 | 36227 | 2014 (2.2) | 25588 (5.2) | 4529 (8.0) |
| 15 minutes | 4529 | 64570 | 36227 | 1132 (4.0) | 18115 (3.6) | 6398 (5.7) |
| 30 minutes | 4027 | 64570 | 36227 | 2014 (2.0) | 22805 (2.8) | 18115 (2.0) |
| 60 minutes | 4027 | 87303 | 36227 | 1600 (2.5) | 25588 (3.4) | 9058 (4.0) |
| 120 minute | 4529 | 81289 | 36227 | 1132 (4.0) | 25588 (3.2) | 6398 (5.7) |

*VC = vehicle control

In the second experiment to determine the dose effect of CMX157 treated HIV-1$_{IIIB}$ on infectivity, concentrated virus is incubated for 15 minutes with eight concentrations ranging from 0.039 to 125 nM of test material and TCID$_{50}$ values are measured by XTT, RT and p24. HDP-ACV is evaluated in parallel to determine if a lipid-nucleotide of similar structure but without HIV activity would have any effect in this assay. The TCID$_{50}$ results of these assays are summarized in Table 7.

Evaluation of CMX157 associated with HIV-1$_{IIIB}$ using lower concentrations of test material yielded a dose response indicating concentrations of 3.9 nM and greater resulted in reduced infectivity. The XTT and p24 endpoints for measuring TCID$_{50}$ yielded greater fold decreases in infectivity compared to the RT endpoint as might be expected for a NRTI in this system. HDP-ACV had no effect on infectious virus when incubated with HIV-1$_{IIIB}$ at the concentrations evaluated.

TABLE 7

TCID$_{50}$ Determination of Treated HIV-1$_{IIIB}$ (15 minutes)

| Drug (nM) | CMX157 (Fold Decrease From VC*) | | | HDP-ACV (Fold Decrease From VC) | | |
|---|---|---|---|---|---|---|
| | XTT Endpoint | RT Endpoint | P24 Endpoint | XTT Endpoint | RT Endpoint | P24 Endpoint |
| 125 | 4027 (4.5) | 64570 (2.5) | 7604 (4.0) | 18115 (0) | 162566 (0) | 21529 (1.4) |
| 39.1 | 5082 (3.6) | 64570 (2.5) | 7604 (4.0) | 16145 (1.1) | 204659 (0) | 30411 (0) |
| 12.5 | 4529 (4.0) | 102336 (1.6) | 5383 (5.6) | 18115 (0) | 144887 (1.1) | 36227 (0) |
| 3.9 | 4529 (4.0) | 102336 (1.6) | 15207 (2.0) | 20325 (0) | 102336 (1.6) | 30411 (0) |

TABLE 7-continued

TCID$_{50}$ Determination of Treated HIV-1$_{IIIB}$ (15 minutes)

| Drug (nM) | CMX157 (Fold Decrease From VC*) | | | HDP-ACV (Fold Decrease From VC) | | |
|---|---|---|---|---|---|---|
| | XTT Endpoint | RT Endpoint | P24 Endpoint | XTT Endpoint | RT Endpoint | P24 Endpoint |
| 1.25 | 9058 (2.0) | 102336 (1.6) | 30411 (0) | 16145 (1.1) | 102336 (1.6) | 21529 (1.4) |
| 0.39 | 12795 (1.4) | 102336 (1.6) | 21529 (1.4) | 20325 (0) | 144887 (1.1) | 30411 (0) |
| 0.125 | 16145 (1.1) | 144887 (1.1) | 30411 (0) | 16145 (1.1) | 102336 (1.6) | 36277 (0) |
| 0.039 | 16145 (1.1) | 157772 (1.0) | 36337 (0) | 18115 (0) | 132749 (1.2) | 30411 (0) |
| 0 | 18115 | 162566 | 30411 | 18155 | 162566 | 30411 |

*VC = vehicle control

Overall, these results indicate CMX157 associates directly with HIV and that this association reduces viral replication. Incubation of HIV with low nanomolar concentrations of CMX157 for short periods of time (1-15 minutes) resulted in decreased viral production in vitro. No effect on viral replication is seen for TFV or the lipid control, HDP-ACV. CMX157 may have advantages over TFV via this mechanism of cell targeting as any HIV exposed to CMX157 will then carry its own antiviral to whatever compartment or cell type it subsequently enters.

The mechanism suggested by the experiments presented here invokes direct association of the CMX157 lipid-TFV drug with HIV followed by delivery of CMX157 by the virus to the cell being infected. The data presented herein demonstrates a significant difference (approximate 300 fold) in the level of CMX157 directly associated with purified HIV versus TFV. Furthermore, pre-incubation of HIV with CMX157 inhibited replication of HIV in cells that are not exposed to drug except via the virus itself; pre-incubation of HIV with TFV has no inhibitory effect on subsequent HIV replication, consistent with the low levels of TFV associated with isolated virions.

This mechanism is distinct from inhibition of natural endogenous reverse transcription (NERT) within HIV virions. Inhibition of NERT has been demonstrated in vitro with high levels of AZT-triphosphate (10 uM) or Nevirapine (NVP) and in vivo with NVP (Zhang 1996, Zhang 2006). While there could be an element of NERT inhibition when cells are treated with CMX157, this mechanism presumably requires formation of TFV-PP which should not occur within isolated virions.

EXAMPLE 3

The anti-HIV-1 activity of CMX157 is evaluated in two-drug combination studies with twenty-four different FDA-approved anti-HIV inhibitors. Each two-drug combination is tested three times in CEM T-lymphocytic cells or MAGI-CCR5 cells acutely infected with the laboratory-adapted strain HIV-1$_{IIIB}$ or HIV-1$_{Ba-L}$, respectively. Viral growth/inhibition is evaluated by measuring virus-induced cytopathic effects (CPE) in CEM cells or by β-galactosidase reporter gene induction in MAGI-CCR5 cells at the experimental endpoint. The cytotoxicity of each two-drug combination is also evaluated in parallel with the antiviral evaluations. The concentrations of CMX157 used in these evaluations are selected in order to test a broad range of concentrations and to provide as complete a dose response curve as possible under the limitations of eight total concentrations. Similarly, the concentrations of lamivudine, abacavir, zidovudine, stavudine, zalcitabine, didanosine, emtricitabine, tenofovir, delavirdine, efavirenz, etravirine, nevirapine, amprenavir, atazanavir, darunavir, indinavir, lopinavir, nelfinavir, ritonavir, saquinavir, tipranavir, maraviroc, enfuvirtide, and raltegravir are selected to provide as complete of a dose response curve as possible under the limitations of five total concentrations. The "positive antagonism control" of d4T (stavudine) in combination with RBV was tested in parallel with each of the assays that were performed. Analysis of drug interactions for each of the two-drug combinations is performed using the Prichard and Shipman MacSynergy II three-dimensional model for statistical evaluation of combination assays. The results from these experiments are summarized in Table 8 and interpretation of the results is provided in Table 9.

For these studies, synergy is defined as drug combinations yielding synergy volumes greater than 50. Slightly synergistic activity and highly synergistic activity have been operationally defined as yielding synergy volumes of 50-100 and >100, respectively. Additive drug interactions have synergy volumes in the range of −50 to 50, while synergy volumes between −50 and −100 are considered slightly antagonistic and those <−100 are highly antagonistic. When assessing interactions at the 50% inhibitory concentrations (IC$_{50}$) for the two drugs, the average dose response from three experiments for each two-drug combination is determined and the IC$_{50}$ range for the two drugs is assessed as the two drug concentrations that bracketed the IC$_{50}$ value (data not shown). If one of the concentrations for a particular drug yields an average percent inhibition of 50%±5%, then this concentration plus the two on either side were included in the IC$_{50}$ range. Subsequently, the interactions within the IC$_{50}$ range of the two drugs were operationally defined as: 1) interactions with synergy volumes >20 is considered synergistic; 2) interactions with synergy volumes in the range of −20 to 20 are considered additive; and 3) interactions with synergy volumes <20 are considered antagonistic.

Overall, CMX-157 is determined to have additive or synergistic interactions for all two-drug combinations performed with FDA-approved antiretroviral drugs. None of the interactions is found to be antagonistic. This conclusion of additive to synergistic interactions for all combinations is also reached when assessing the interactions at the IC$_{50}$ range of the two drugs from each combination. In contrast, the positive antagonism control of stavudine in combination with ribavirin resulted in antagonistic interactions as expected.

TABLE 8

Antiviral Efficacy of CMX157 in Combination with Approved Antiretrovirals in CEM and MAGI-CCR5 Cells (95% Confidence Values)

| Compound | Synergy/Antagonism Volume ($nM^2$ %, $\mu M^2$ % or $nM\mu M$ %)[1] | | | Mean Synergy/Antagonism Volume ($nM^2$ %, $\mu M^2$ % or $nM\mu M$ %; n = 3)[2] |
|---|---|---|---|---|
| | Result 1 | Result 2 | Result 3 | |
| Nucleoside Reverse Transcriptase Inhibitors (NRTI) | | | | |
| Lamivudine (3TC) | 87.5/−42.6 | 51.8/0 | 79.0/0 | 69.8/−11.3 |
| Abacavir (ABC) | 25.1/−35.8 | 0/−2.32 | 19.7/−12.1 | 14.9/−16.7 |
| Zidovudine (AZT) | 5.01/−67.8 | 32.7/0 | 0/−0.77 | 11.5/−21.7 |
| Stavudine (d4T) | 4.47/0 | 40.6/0 | 0.39/−1.83 | 15.2/−0.61 |
| Zalcitabine (ddC) | 154/0 | 80.0/0 | 131/−15.9 | 122/−5.29 |
| Didanosine (ddI) | 3.38/−1.01 | 3.04/0 | 29.6/0 | 12.0/−0.34 |
| Emtricitabine (FTC) | 61.5/0 | 72.0/0 | 84.1/0 | 72.5/0 |
| Tenofovir (TFV) | 17.6/−0.53 | 37.2/0 | 30.3/0 | 28.4/−0.18 |
| Non-Nucleoside Reverse Transcriptase Inhibitors (NNRTI) | | | | |
| Delavirdine (DLV) | 152/0 | 68.4/0 | 1.01/−2.58 | 72.9/0 |
| Efavirenz (EFV) | 85.7/0 | 80.6/0 | 43.2/0 | 69.8/0 |
| Etravirine (ETV) | 34.9/−0.75 | 106/0 | 67.4/−0.87 | 69.0/−0.29 |
| Nevirapine (NVP) | 74.1/0 | 41.5/0 | 0/0 | 38.5/0 |
| Protease Inhibitors (PI) | | | | |
| Amprenavir (APV) | 104/0 | 43.1/0 | 7.31/0 | 51.4/0 |
| Atazanavir (AW) | 104/0 | 67.4/0 | 12.7/−0.72 | 61.5/−0.24 |
| Darunavir (DRV) | 109/0 | 11.5/−2.31 | 9.48/0 | 43.2/−0.54 |
| Indinavir (IDV) | 78.7/−0.56 | 62.7/0 | 17.6/0 | 53.0/−0.19 |
| Lopinavir (LPV) | 78.8/−0.31 | 28.3/0 | 59.8/−0.12 | 55.6/−0.14 |
| Nelfinavir (NFV) | 32.1/0 | 85.1/0 | 125/0 | 80.9/0 |
| Ritonavir (RTV) | 47.5/0 | 38.0/0 | 116/−2.61 | 66.4/0 |
| Saquinavir (SQV) | 123/−2.54 | 8.35/−0.81 | 3.93/0 | 45.2/−1.12 |
| Tipranavir (TPV) | 110/0 | 29.4/−8.60 | 16.8/0 | 52.2/−2.87 |
| Entry Inhibitors | | | | |
| Maraviroc (MVC)[3] | 145/−3.82 | 14.1/−3.12 | 96.6/0 | 85.3/−2.31 |
| Enfuvirtide (T-20) | 0/0 | 3.05/0 | 0/0 | 1.02/0 |
| Integrase Inhibitor | | | | |
| Raltegravir (RAL) | 18.4/0 | 1.92/0 | 82.6/0 | 34.3/0 |

[1]The MacSynergy II program takes the raw data from individual experiments and calculates a positive (synergy) or negative (antagonism) value for each drug-drug combination. Positive values are summed to give a Volume of Synergy and negative values are summed to give a Volume of Antagonism (both values are reported for each experiment).
[2]The Antiviral Synergy Plot (95%) datasets from multiple experiments (n = 3) are combined and arithmetic means are calculated for each drug-drug concentration. The positive and negative values are individually summed to respectively give Mean Volumes for synergistic and antagonistic interactions.
[3]The antiviral efficacy results of CMX157 in combination with Maraviroc were performed in MAGI-CCR5 cells. All other evaluations were performed in CEM-SS cells.

TABLE 9

Interpretation of the MacSynergy Analysis for the Antiviral Efficacy of CMX157 in Combination with Approved Antiretroviral Drugs

| Antiretroviral Drug | Interpretation of Antiviral Results |
|---|---|
| Nucleoside Reverse Transcriptase Inhibitors (NRTI) | |
| Lamivudine (3TC) | Slightly Synergistic |
| Abacavir (ABC) | Additive |
| Zidovudine (AZT) | Additive |
| Stavudine (d4T) | Additive |
| Zalcitabine (ddC) | Highly Synergistic |
| Didanosine (ddI) | Additive |
| Emtricitabine (FTC) | Slightly Synergistic |
| Tenofovir (TFV) | Additive |
| Non-Nucleoside Reverse Transcriptase Inhibitors (NNRTI) | |
| Delavirdine (DLV) | Slightly Synergistic |
| Efavirenz (EFV) | Slightly Synergistic |
| Etravirine (ETV) | Slightly Synergistic |
| Nevirapine (NVP) | Additive |
| Protease Inhibitors (PI) | |
| Amprenavir (APV) | Slightly Synergistic |
| Atazanavir (ATV) | Slightly Synergistic |
| Darunavir (DRV) | Additive |
| Indinavir (IDV) | Slightly Synergistic |
| Lopinavir (LPV) | Slightly Synergistic |
| Nelfinavir (NFV) | Slightly Synergistic |
| Ritonavir (RTV) | Slightly Synergistic |
| Saquinavir (SQV) | Additive |
| Tipranavir (TPV) | Slightly Synergistic |
| Entry Inhibitors | |
| Maraviroc (MVC) | Slightly Synergistic |
| Enfuvirtide (T-20) | Additive |
| Integrase Inhibitor | |
| Raltegravir (RAL) | Additive |
| Positive Antagonism Control (CEM-SS Cells) | |
| Stavudine/Ribavirin (d4T/RBV) | Highly Antagonistic at expected concentrations |

TABLE 9-continued

Interpretation of the MacSynergy Analysis for the Antiviral Efficacy of CMX157 in Combination with Approved Antiretroviral Drugs

| Antiretroviral Drug | Interpretation of Antiviral Results |
|---|---|
| Positive Antagonism Control (MAGI-CCR5 Cells) | |
| Stavudine/Ribavirin (d4T/RBV) | Highly Antagonistic at expected concentrations |

No antagonistic interactions were observed within the concentration ranges examined for antiviral efficacy between CMX157 and the twenty-four FDA-approved antiretroviral drugs. A highly synergistic interaction is observed between CMX157 and zalcitabine, and slightly synergistic interactions were observed with lamivudine, emtricitabine, delavirdine, efavirenz, etravirine, amprenavir, atazanavir, indinavir, lopinavir, nelfinavir, ritonavir, tipranavir, and maraviroc, suggesting possible beneficial interactions with these drugs. CMX157 interactions with the remaining drugs resulted in strictly additive results. In contrast, the positive antagonism control of stavudine in combination with Ribavirin exhibited a highly antagonistic interaction in all experiments (mean antagonism volume=−330 $\mu M^2$% in CEM cells and −111 $\mu M^2$% in MAGI-R5 cells). Therefore, the overall interpretation of these data suggest that antagonism of the antiviral effects of the twenty-four FDA-approved antiretroviral drugs evaluated in this study should not be a problematic issue associated with the use of CMX157 in a clinical setting.

It is important to note there was no evidence of synergistic cytotoxicity within the drug concentrations examined for CMX157 (10 μM=highest test concentration). This is not unexpected because none of the drugs are cytotoxic within the concentration ranges evaluated. Much higher concentrations of all drugs (around the $TC_{50}$ concentration) would be required to correctly examine potential synergistic cytotoxicity interactions. However, it is important to document there are no notable synergistic cytotoxicities observed at concentrations where the FDA-approved drugs display potent antiviral properties.

EXAMPLE 4

The signature mutation for tenofovir (TFV) is K65R, which is generally associated with a 2 to 4 fold increase in $IC_{50}$ for tenofovir and lack of clinical response to Viread. In vitro studies designed to select CMX157 resistant mutants use wild-type HIV-1 as the primary inoculum and TFV as a positive control. These studies are conducted by serial passage of HIV-1$_{IIIB}$ and HIV-1RF in CEM-SS cells using increasing concentrations of TFV or CMX157. Drug levels are increased following detection of viral growth at each passage using procedures known to one skilled in the art. Upon completion of each passage, the reverse transcriptase coding region of the viral genome is sequenced to identify any possible resistance-associated mutations that may have emerged within the virus pool.

As show in Tables 10 and 11, there is no resistance to CMX157 through 9 passages. In contrast, K65R was selected by TFV by passage 8. These data indicates it may be more difficult for HIV to develop resistance to CMX157 than to TFV.

TABLE 10

Passaging of HIV-1$_{IIIB}$ in CMX157

| Passage | CMX157 Passaging Concentration (Fold above $IC_{50}$) | Day of Peak Virus Production[a] (RT activity) | Mutations Observed in RT of Passaged Virus[b] | Comments |
|---|---|---|---|---|
| 1 | 300 nM (2× $IC_{50}$) | Day 6 (23,615 cpm) | None | Robust virus replication observed |
| 2 | 600 nM (4× $IC_{50}$) | Day 6 (6,706 cpm) | None | Reduced virus replication observed |
| 3 | 900 nM (6× $IC_{50}$) | Day 14 (11,364 cpm) | None | Moderate virus replication observed |
| 4 | 1,200 nM (8× $IC_{50}$) | Day 6 (34,440 cpm) | None | Robust virus replication observed |
| 5 | 1,800 nM (12× $IC_{50}$) | Day 6 (14,061 cpm) | None | Moderate virus replication observed |
| 6 | 2,400 nM (16× $IC_{50}$) | Day 7 (9,933 cpm) | T215I mix (minor population) | Low-level to moderate virus replication observed; minor mix of T215I unlikely to be associated with resistance to CMX157 (not observed in passage 7) |
| 7 | 2,800 nM (19× $IC_{50}$) | Day 5 (1,900 cpm) | None | Low-level virus replication observed through 16 days in culture; continue with passage 8 using same concentration in order to allow virus to grow out |
| 8 | 2,800 nM (19× $IC_{50}$) | Day 9 (18,638 cpm) | Minor, mixed populations observed: E122K, T200I, Q207E, P272A, R277K, I293V, P294Q, E297K, and T400A | Relatively robust virus replication observed; minor mixes of amino acids observed unlikely to be associated with resistance to CMX157, these changes are reported based on small peak heights observed in the chromatograms, however most of these small peaks are likely to be artifacts of the sequencing |

TABLE 10-continued

Passaging of HIV-1$_{IIIB}$ in CMX157

| Passage | CMX157 Passaging Concentration (Fold above IC$_{50}$) | Day of Peak Virus Production[a] (RT activity) | Mutations Observed in RT of Passaged Virus[b] | Comments |
|---|---|---|---|---|
| 9 | 5,600 nM (36× IC$_{50}$) | Day 11 (1,585 cpm) | Minor, Mixed Populations observed: E122K, D123E, T200I, Q207E, R211K, P272A, R277K, I293V, P294Q, E297K, I375V, T400A, N519S, A554T | Low level virus replication observed through 13 days in culture; RT activity peaked at day 11 and dropped off on days 12 and 13. Therefore, day 11 supernatant was used, even though the RT activity is still relatively low at 1,585 cpm. Minor mixes of amino acids present; unlikely to be associated with resistance to CMX157 |

[a]Day post-infection when greatest level of virus was observed based on RT activity

[b]minor = mutation is minor population in mix; major = mutation is major population; equal = equal peak heights N/A = not applicable (virus replication not observed or RT not sequenced)

TABLE 11

Passaging of HIV-1$_{IIIB}$ in Tenofovir

| Passage | Tenofovir Passaging Concentration (Fold above IC$_{50}$) | Day of Peak Virus Production[a] (RT activity) | Mutations Observed in RT of Passaged Virus[b] | Comments |
|---|---|---|---|---|
| 1 | 10 μM (2× IC$_{50}$) | Day 6 (3,525 cpm) | None | Low-level virus replication observed |
| 2 | 20 μM (4× IC$_{50}$) | Day 7 (2,016 cpm) | None | Low-level virus replication observed |
| 3 | 30 μM (6× IC$_{50}$) | Day 14 (2,062 cpm) | None | Low-level virus replication observed |
| 4 | 40 μM (8× IC$_{50}$) | Day 6 (3,109 cpm) | None | Low-level virus replication observed |
| 5 | 40 μM (8× IC$_{50}$) | Day 14 (1,788 cpm) | None | Low-level virus replication observed; continue with passage 6 using same concentration in order to allow virus to grow out |
| 6 | 40 μM (8× IC$_{50}$) | Day 19 (23,508) | None | Robust virus replication observed; apparent significant increase in replication compared to passages 1-5 |
| 7 | 45 μM (9× IC$_{50}$) | Day 7 (24,408 cpm) | E300D mix (minor population) | Robust virus replication observed; minor mix of E300D unlikely to be associated with resistance to tenofovir (not observed in passage 8) |
| 8 | 50 μM (10× IC$_{50}$) | Day 9 (57,455 cpm) | E404D mix (minor) G436E mix (minor) | Robust virus replication observed; E404D and G436E changes possibly associated with resistance selection by tenofovir |
| 9 | 55 μM (11× IC$_{50}$) | Day 11 (25,458 cpm) | K65R mix (equal) E404D mix (major) G436E mix (minor) | Robust virus replication observed; prototypical tenofovir resistance mutation K65R starting to emerge; E404D and G436E mutations appear to be associated with tenofovir resistance |
| 10 | 60 μM (12× IC$_{50}$) | Day 7 (31,549 cpm) | K65R mix (major) E404D mix (minor) G436E mix (minor) | Robust virus replication observed; prototypical tenofovir resistance mutation K65R = major population; E404D and G436E mutations appear to be associated with tenofovir resistance |

[a]Day post-infection when greatest level of virus was observed based on RT activity

[b]minor = mutation is minor population in mix; major = mutation is major population; equal = equal peak heights N/A = not applicable (virus replication not observed or RT not sequenced)

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method of treating a subject for human immunodeficiency virus (HIV) and/or hepatitis B virus (HBV) infection, wherein the subject has not been previously administered an antiviral active agent for said HIV or HBV infection, the method comprising:

concurrently administering to the subject an antiviral compound of the Formula:

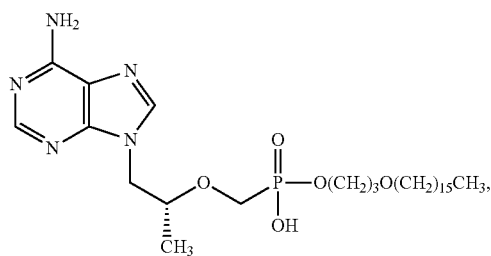

or a pharmaceutically acceptable salt thereof and zalcitabine; in an amount effective to treat the HIV and/or HBV infection.

2. The method of claim 1, wherein said subject is immunocompromised.

3. The method of claim 1, wherein said virus is HBV and not HIV.

4. The method of claim 1, wherein said subject is infected with both HBV and HIV, and said antiviral compound is administered in an amount effective to treat both said HBV and HIV.

5. The method of claim 1, wherein said subject is in utero and said antiviral compound is administered to a mother carrying said subject in utero.

6. A method of treating a subject for human immunodeficiency virus (HIV) and/or hepatitis B virus (HBV) infection, wherein said subject has developed resistance or a toxic response to at least one other antiviral compound in response to prior administration of said at least one other antiviral compound to said subject for said HIV or HBV infection, the method comprising: concurrently administering to said subject an antiviral compound of the Formula:

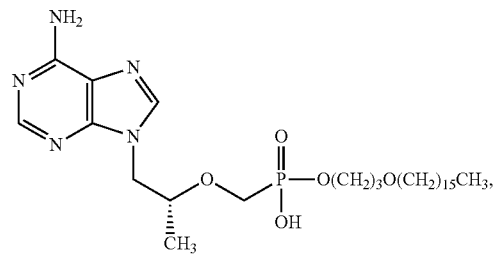

or a pharmaceutically acceptable salt thereof and zalcitabine; in an amount effective to treat the HIV and/or HBV infection.

7. The method of claim 6, wherein the virus is HBV and not HIV.

8. The method of claim 6, wherein said subject is infected with both HBV and HIV, and said antiviral compound is administered in an amount effective to treat both said HBV and HIV.

9. The method of claim 6, wherein said subject is in utero and said antiviral compound is administered to a mother carrying said subject in utero.

10. A pharmaceutical composition comprising: (a) an antiviral compound of the Formula:

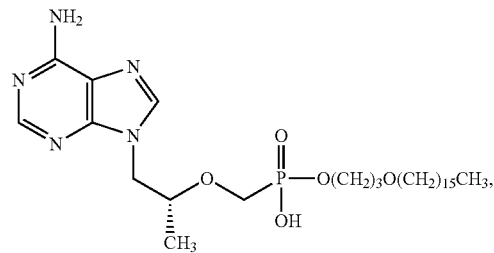

or a pharmaceutically acceptable salt thereof;
(b) zalcitabine; and
(c) a pharmaceutically acceptable carrier.

11. A method of treating a subject for human immunodeficiency virus (HIV) and/or hepatitis B virus (HBV) infection, wherein the subject has not been previously administered an antiviral active agent for said HIV or HBV infection, the method comprising:

administering to the subject an antiviral compound of the formula:

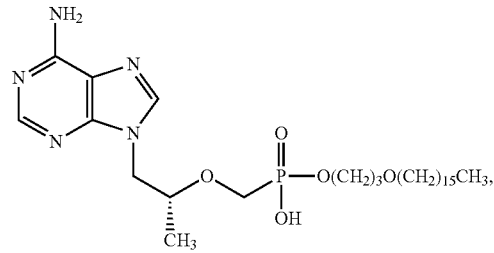

or a pharmaceutically acceptable salt thereof, followed by administering to the subject zalcitabine;

wherein both the antiviral compound and zalcitabine are administered in an amount effective to treat the HIV and/or HBV infection.

12. A method of treating a subject for human immunodeficiency virus (HIV) and/or hepatitis B virus (HBV) infection, wherein the subject has not been previously administered an antiviral active agent for said HIV or HBV infection, the method comprising:

administering to the subject zalcitabine, followed by administering to the subject an antiviral compound of the formula:

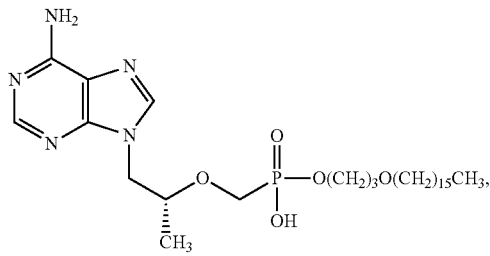

wherein both the antiviral compound and zalcitabine are administered in an amount effective to treat the HIV and/or HBV infection.

13. A method of treating a subject for human immunodeficiency virus (HIV) and/or hepatitis B virus (HBV) infection, wherein said subject has developed resistance or a toxic response to at least one other antiviral compound in response to prior administration of said at least one other antiviral compound to said subject for said HIV or HBV infection, the method comprising:

administering to said subject an antiviral compound of the Formula:

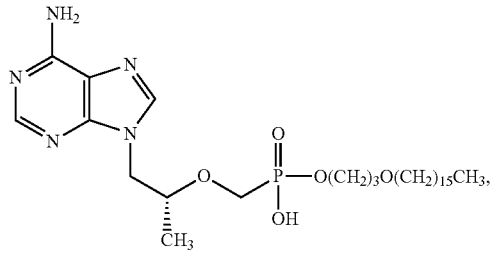

or a pharmaceutically acceptable salt thereof, followed by administering to the subject zalcitabine;

wherein both the antiviral compound and zalcitabine are administered in an amount effective to treat the HIV and/or HBV infection.

14. A method of treating a subject for human immunodeficiency virus (HIV) and/or hepatitis B virus (HBV) infection, wherein said subject has developed resistance or a toxic response to at least one other antiviral compound in response to prior administration of said at least one other antiviral compound to said subject for said HIV or HBV infection, the method comprising:

administering to the subject zalcitabine, followed by administering to the subject an antiviral compound of the formula:

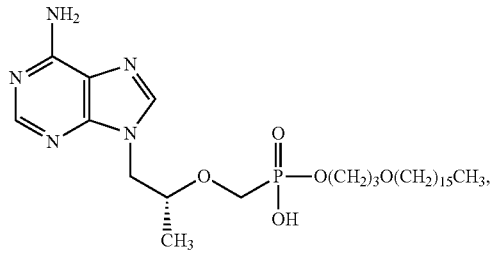

wherein both the antiviral compound and zalcitabine are administered in an amount effective to treat the HIV and/or HBV infection.

* * * * *